(12) United States Patent
Nakayama et al.

(10) Patent No.: US 8,172,155 B2
(45) Date of Patent: May 8, 2012

(54) THERMAL SENSATION DETERMINING APPARATUS AND METHOD, AND AIR-CONDITIONING CONTROL APPARATUS USING THERMAL SENSATION DETERMINATION RESULT

(75) Inventors: Kanako Nakayama, Yokohama (JP); Takuji Suzuki, Yokohama (JP); Kazushige Ouchi, Saitama (JP); Kenichi Kameyama, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1032 days.

(21) Appl. No.: 12/046,167

(22) Filed: Mar. 11, 2008

(65) Prior Publication Data

US 2008/0243027 A1    Oct. 2, 2008

(30) Foreign Application Priority Data

Mar. 27, 2007   (JP) ................ 2007-082701

(51) Int. Cl.
*F23N 5/20* (2006.01)
*G05D 23/00* (2006.01)
*F24F 3/14* (2006.01)
*G01K 3/00* (2006.01)

(52) U.S. Cl. ............. 236/46 R; 236/44 C; 374/112
(58) Field of Classification Search .......... 236/46 R, 236/44 C, 49.3, 91 C; 374/112; 600/549
See application file for complete search history.

(56) References Cited

FOREIGN PATENT DOCUMENTS

| JP | PH06-265189 | 9/1994 |
| JP | 8128694 | 5/1996 |
| JP | 11190545 | 7/1999 |
| JP | 2006194540 | 7/2006 |
| WO | WO 2007/007632 | 1/2007 |
| WO | WO 2007007632 A1 * | 1/2007 |

OTHER PUBLICATIONS

Nakayama et al., "Thermal sensation measurement from biologic signals", The Institute of Electronics, Information and Communication Engineers (IEICE) Technical Report, vol. 105, Mar. 2006, 6 pps.*
Ishiguro, et al., "*Indoor climate for comfortable sleep, considering heat and moisture transfer between a bedroom, bedding and a human body: Air control system using a predictive model for thermal comfort*", The Third International Conference on Human-Environment System ICHES'06 in Tokyo, Japan, Sep. 12-15, 2005, pp. 139-144.
Mori, et al., "*Experimental Study on Thermal Sensation Index in Thermal Transiets*", Journal of Architecture, Planning and Environmental Engineering, vol. 563, Jan. 9-15, 2003, 7 pps.
Nakayama, et al., "*Thermal sensation measurement from biologic signals*", The Institute of Electronics, Information and Communication Engineers (IEICE) Technical Report, vol. 105, Mar. 2006, 6 pps.
Official action for corresponding Japanese application No. 2007-082701 dated Jan. 13, 2009 (with translation).

* cited by examiner

*Primary Examiner* — Chen Wen Jiang
(74) *Attorney, Agent, or Firm* — Ohlandt, Greeley, Ruggiero & Perle, L.L.P.

(57) ABSTRACT

A thermal sensation determining apparatus includes a skin temperature detecting unit configured to detect a skin temperature of a peripheral site of a subject's body, a variation state determining unit configured to determine a variation state of the skin temperature during a first interval to obtain a variation state determination result, a gradient detecting unit configured to detect a gradient of the skin temperature during a second interval to determine the gradient to obtain a gradient detection result, and a thermal sensation determining unit configured to determine the subject's thermal sensation using the variation state determination result and the gradient detection result to obtain a thermal sensation determination result classified into levels ranging from "hot" to "cold" based on a "moderate" temperature.

8 Claims, 15 Drawing Sheets

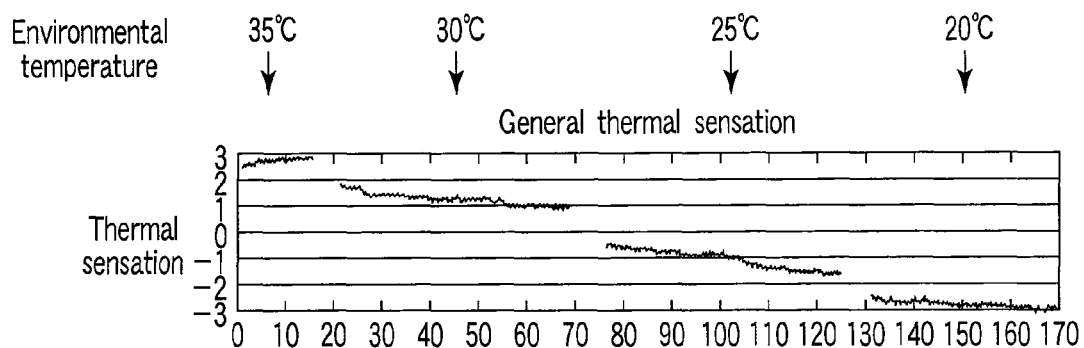
F I G. 3A
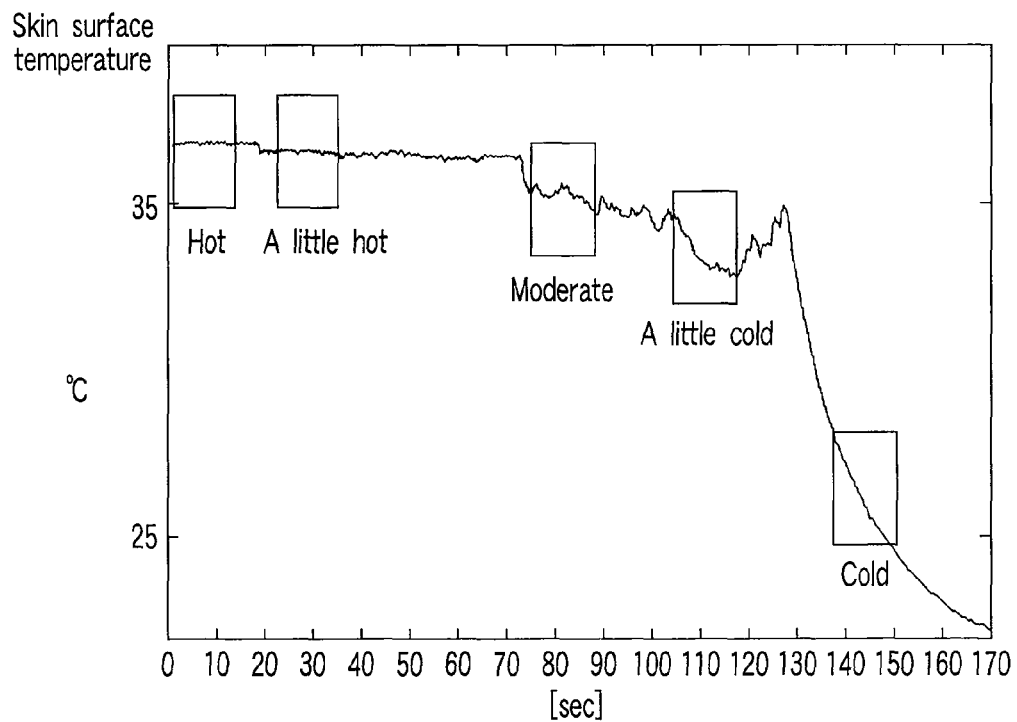
F I G. 3B

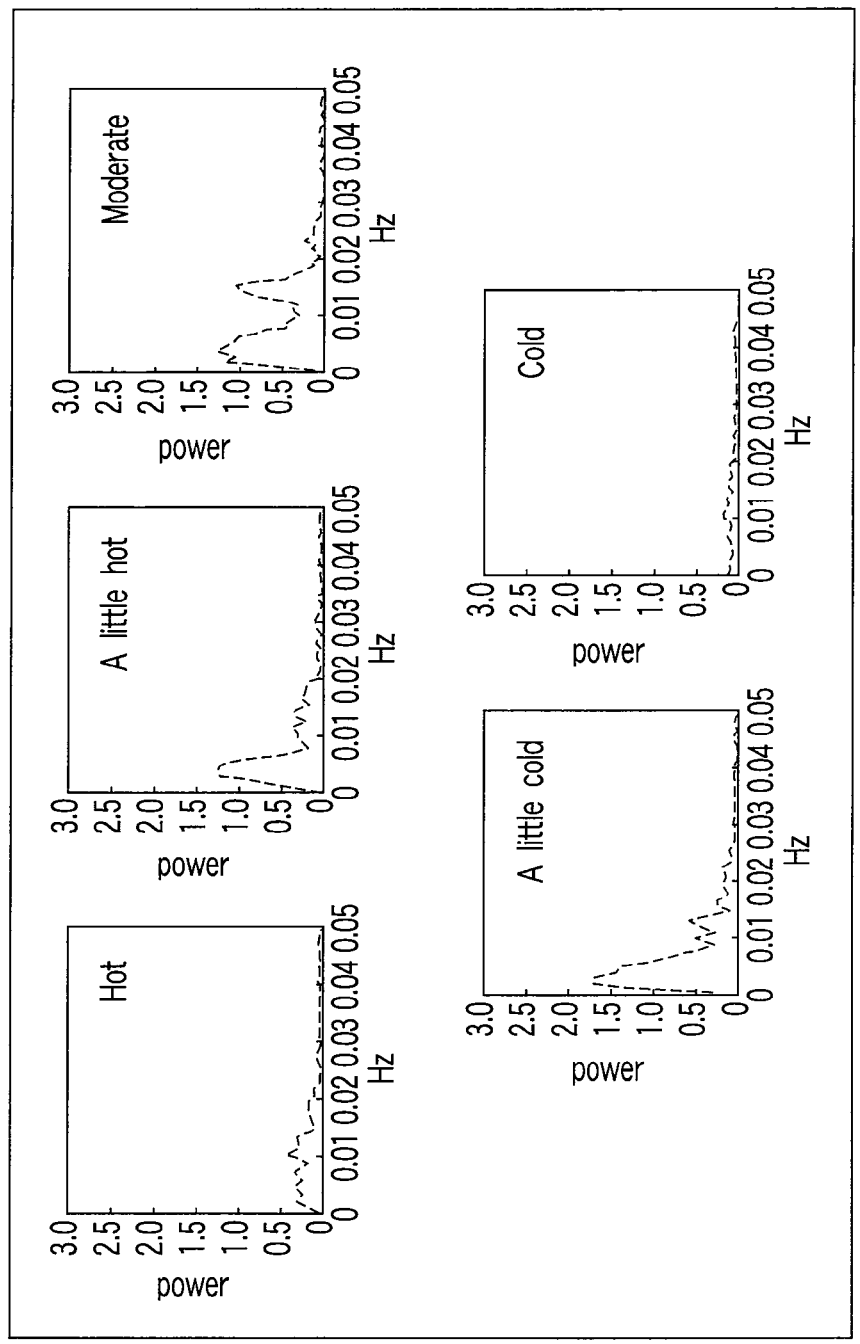
F I G. 3C

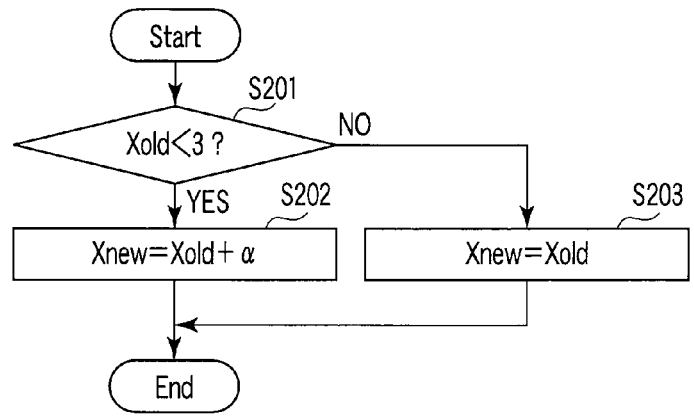
F I G. 4
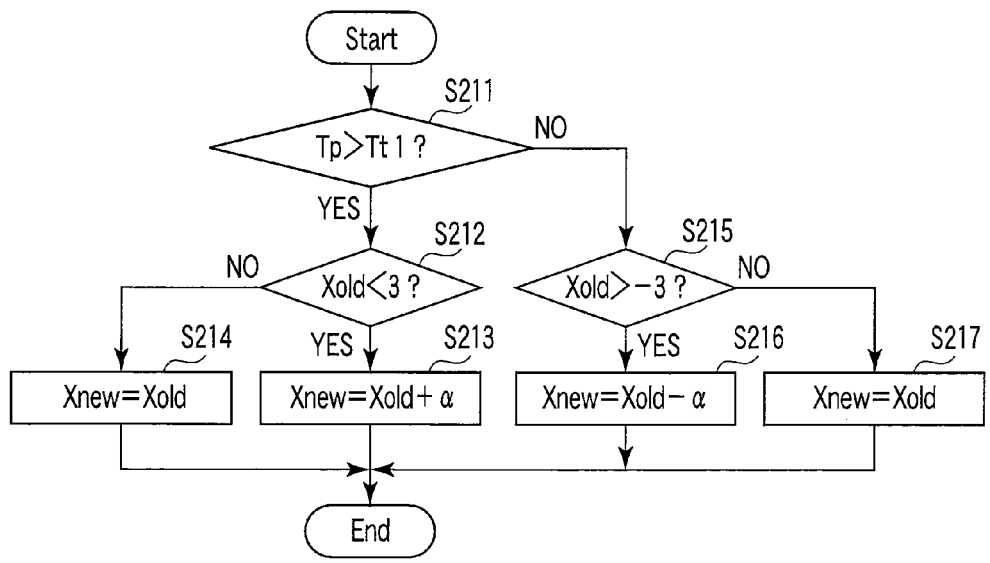
F I G. 5

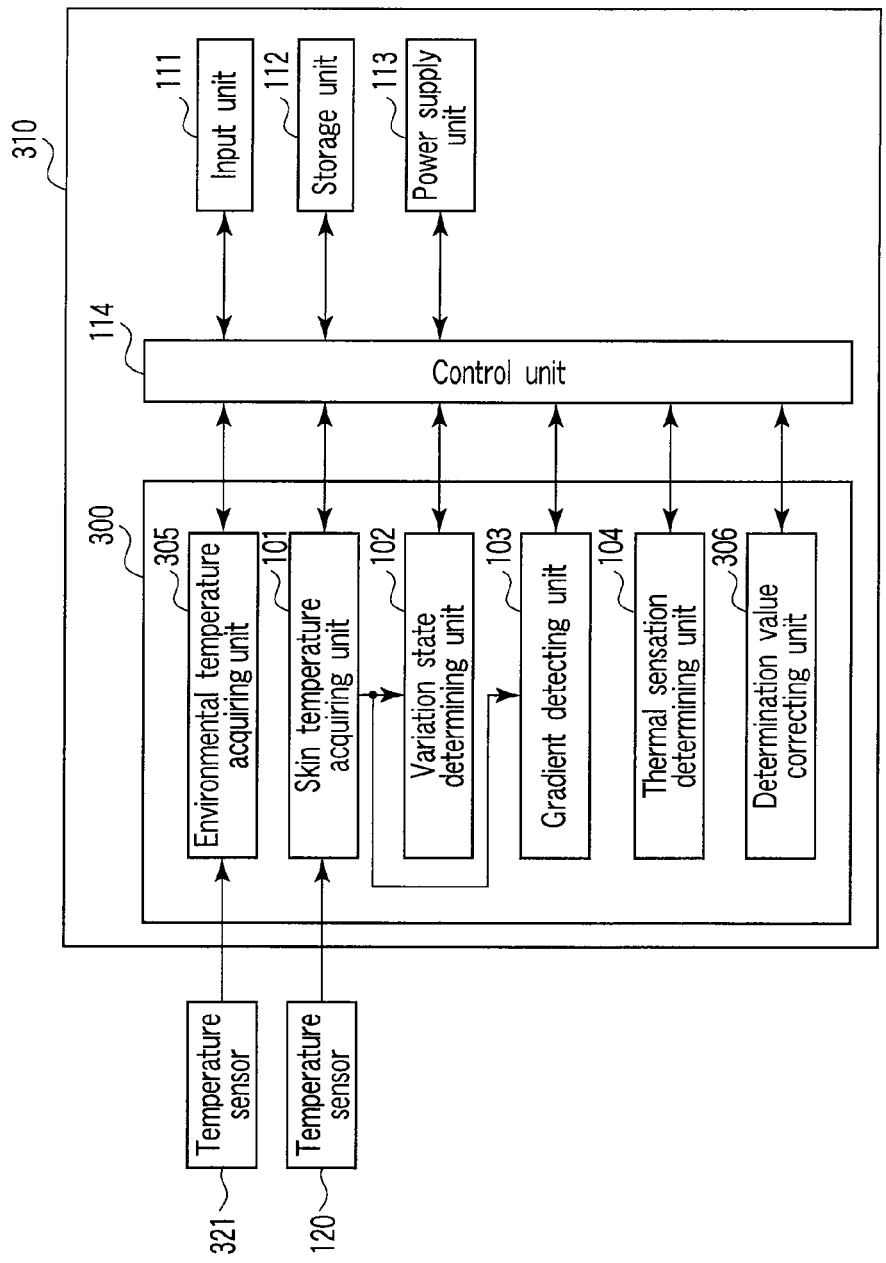
F I G. 13

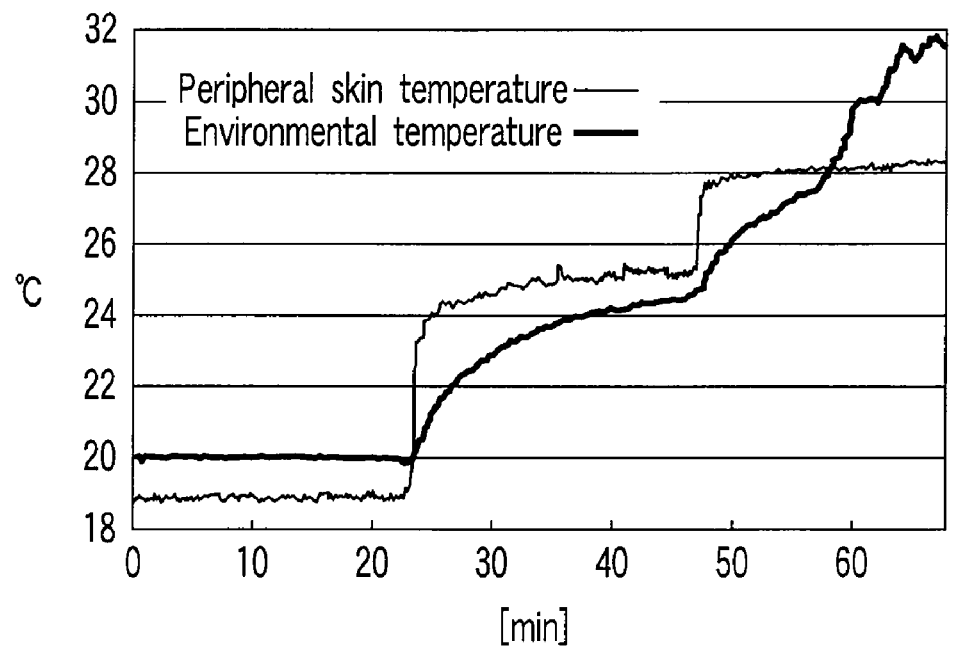
F I G. 14A
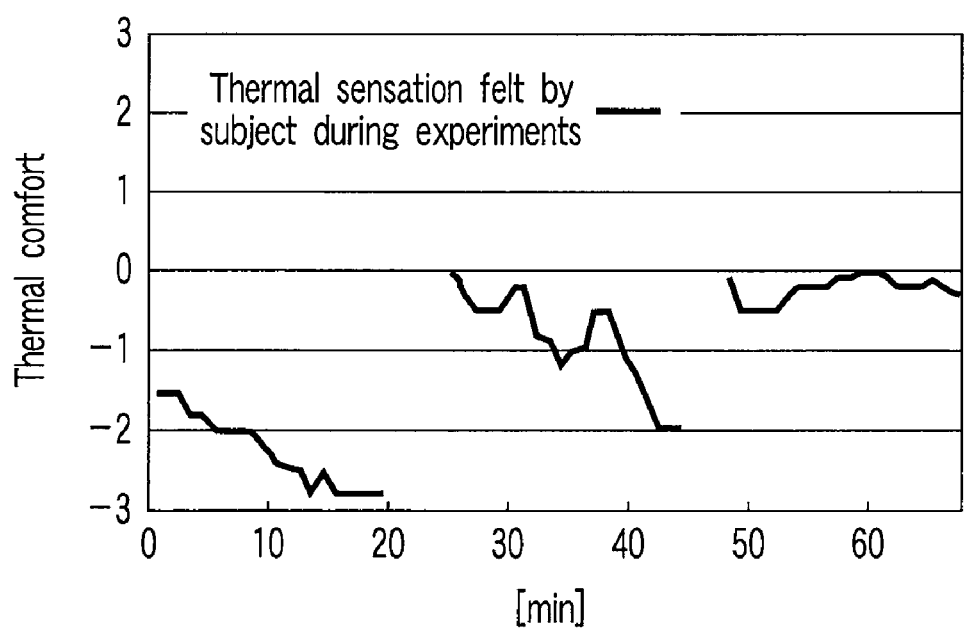
F I G. 14B

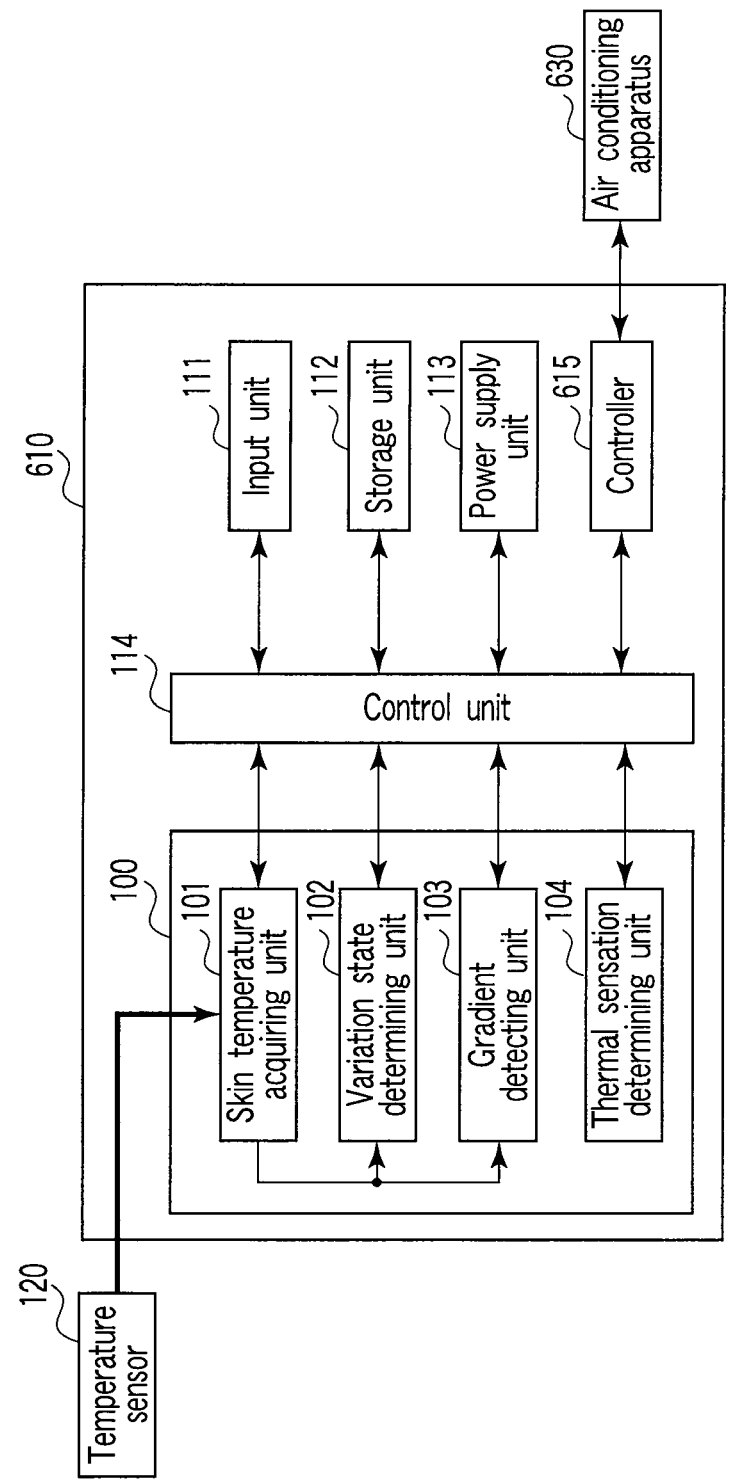
F I G. 18

THERMAL SENSATION DETERMINING APPARATUS AND METHOD, AND AIR-CONDITIONING CONTROL APPARATUS USING THERMAL SENSATION DETERMINATION RESULT

CROSS-REFERENCE TO RELATED APPLICATIONS

This application is based upon and claims the benefit of priority from prior Japanese Patent Application No. 2007-082701, filed Mar. 27, 2007, the entire contents of which are incorporated herein by reference.

BACKGROUND OF THE INVENTION

1. Field of the Invention

The present invention relates to a thermal sensation determining apparatus and method utilizing a biological index obtained from a subject, and an air-conditioning control apparatus and method using the thermal sensation determination result.

2. Description of the Related Art

An apparatus that determines a subject's thermal sensation using thermal indices such as SET* (Standard Effective Temperature) and PMV (Predicted Mean Vote) have hitherto been known. However, the use of SET* and PMV requires measuring instruments for measuring environmental indices such as a temperature, air current, radiant heat, the amount of clothing, and the quantity of work. On the other hand, techniques have been studied which detect and analyze the subject's biological index to relatively easily determine the subject's thermal sensation without using environmental indices.

Skin temperature is often used as a biological index for determination of the subject's thermal sensation. For example, in A. Ishiguro et al., "Indoor climate for comfortable sleep, considering head and moisture transfer between a bedroom, bedding and a human body: Air control system using a predictive model for thermal comfort", The Third International Conference on Human Environment Systems (ICHES'05), Tokyo, September 2005 (related art 1), and I. Mori et al., "Discussions of thermal sensation prediction for a non-steady state based on experiments", a collection of papers from Planning Section of Architectural Institute of Japan, January 2003, No. 563, p 9 to 15 (related art 2), thermal sensation prediction formulae are proposed which are obtained on the basis of experimental values for average skin temperature, deep body temperature, and skin surface heat current measured at seven to eight measurement points so that the subject's thermal sensation can be determined on the basis of the thermal sensation prediction formulae. The subject's thermal sensation is determined on the basis of the prediction formulae. Furthermore, the technique described in JP-A H06-265189 (KOKAI) determines the thermal sensation on the basis of the skin temperature measured, every 10 minutes, at 10 measurement points set in partial areas of the human body, such as the sole. Additionally, in K. Nakayama et al., "Thermal sensation measurement using biological signals", a technical research report from The Institute of Electronics, Information and Communication Engineers, March 2006, vol. 105, No. 682, p 55 to 59 (related art 3), the thermal sensation is determined to be at one of three levels, "hot", "comfortable", and "cold", on the basis of a fluctuation in measured skin temperature and an absolute temperature.

Techniques have also been studied which use the above-described thermal sensation determination results to perform air-conditioning control to automatically set an air-conditioning control environment so that the subject feels comfortable.

With the techniques described in the related art 1 and the related art 2, a plurality of temperature sensors need to be installed on the subject's body in order to measure the average skin temperature and the skin surface heat current. A thermometer further needs to be inserted into the body in order to measure the deep body temperature. Furthermore, the technique described in JP-A H06-265189 (KOKAI) necessarily requires a large-sized apparatus configuration because of the need to measure the temperature at 10 measurement points. Additionally, the technique described in the related art 3 can determine the thermal sensation only at three levels and thus provide only rough determination results. Therefore, these techniques cannot easily determine the thermal sensation or provide detailed determination results. It is thus difficult, using such techniques, to perform precise air-conditioning control on a daily basis.

BRIEF SUMMARY OF THE INVENTION

According to an aspect of the invention, there is provided a thermal sensation determining apparatus comprising: a skin temperature detecting unit configured to detect a skin temperature of a peripheral site of a subject's body; a variation state determining unit configured to determine a variation state of the skin temperature during a first interval to be a first state in which the variation in skin temperature is the most moderate, a second state in which the variation is more significant than that in the first state, or a third state in which the variation is more significant than that in the second state, to obtain a variation state determination result; a gradient detecting unit configured to detect a gradient of the skin temperature during a second interval to determine the gradient to be a first gradient which is the greatest, a second gradient which is smaller than the first gradient, and a third gradient which is smaller than the second gradient, to obtain a gradient detection result; and a thermal sensation determining unit configured to determine the subject's thermal sensation using the variation state determination result and the gradient detection result to obtain a thermal sensation determination result classified into levels ranging from "hot" to "cold" based on a "moderate" temperature.

According to an another aspect of the invention, there is provided an air-conditioning control apparatus comprising: a skin temperature detecting unit configured to detect a skin temperature of a peripheral site of a subject's body; a variation state determining unit configured to determine a variation state of the skin temperature during a first interval to be a first state in which the variation in skin temperature is the most moderate, a second state in which the variation is more significant than that in the first state, or a third state in which the variation is more significant than that in the second state, to obtain a variation state determination result; a gradient detecting unit configured to detect a gradient of the skin temperature during a second interval to determine the gradient to be a first gradient which is the greatest, a second gradient which is smaller than the first gradient, and a third gradient which is smaller than the second gradient, to obtain a gradient detection result; a thermal sensation determining unit configured to determine the subject's thermal sensation using the variation state determination result and the gradient detection result to obtain a thermal sensation determination result classified into levels ranging from "hot" to "cold" based on a "moderate" temperature; and a controller to control turning-on and -off of an air-conditioning apparatus based on the thermal sensation determination result.

The present invention provides a thermal sensation determining apparatus and method easily providing a detailed thermal sensation determination result, and an air-conditioning control apparatus and method using the thermal sensation determination result.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

FIG. 3A is a graph showing thermal sensation felt by a subject when an environmental temperature is varied from 35° C. to 20° C.;

FIG. 3B is a graph showing a variation in the subject's skin temperature corresponding to FIG. 3A;

FIG. 3C is a graph showing the results of the frequency analysis of a variation in skin temperature in a specified area in FIG. 3B;

FIG. 4 is a flowchart showing a determining operation performed by a thermal sensation determining unit shown in FIG. 1 when a periodic variation is in a first state and a temperature gradient is a first gradient;

FIG. 5 is a flowchart showing a determining operation performed by the thermal sensation determining unit shown in FIG. 1 when the periodic variation is in the first state and the temperature gradient is a second gradient;

FIG. 13 is a block diagram showing a thermal sensation determining apparatus according to a second embodiment;

FIG. 14A is a graph showing a variation in the subject's peripheral skin temperature measured when the environmental temperature is varied;

FIG. 14B is a graph corresponding to FIG. 14A and showing the subject's thermal sensation;

FIG. 18 is a block diagram showing an air-conditioning control system according to a fourth embodiment.

DETAILED DESCRIPTION OF THE INVENTION

Embodiments of the present invention will be described below with reference to the drawings.

First Embodiment

Figure 1:
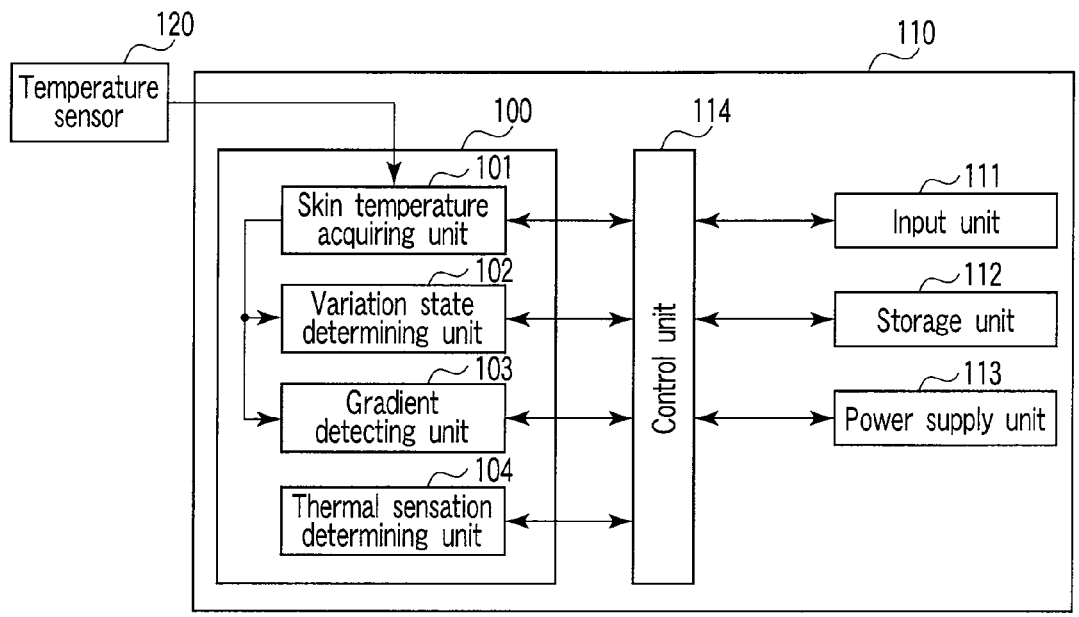
FIG. 1 is a block diagram showing a thermal sensation determining apparatus according to a first embodiment.

As shown in FIG. 1, a thermal sensation determining apparatus 100 according to a first embodiment of the present invention has a skin temperature acquiring unit 101, a variation state determining unit 102, a gradient detecting unit 103, and a thermal sensation determining unit 104. The thermal sensation determining apparatus 100 is incorporated in a thermal sensation determining system 110. The thermal sensation determining system 110 has an input unit 111, a storage unit 112, a power supply unit 113, and a control unit 114. A temperature sensor 120 is connected to the thermal sensation determining system 110 to measure the skin temperature of a peripheral part of a subject's body.

Figure 2:
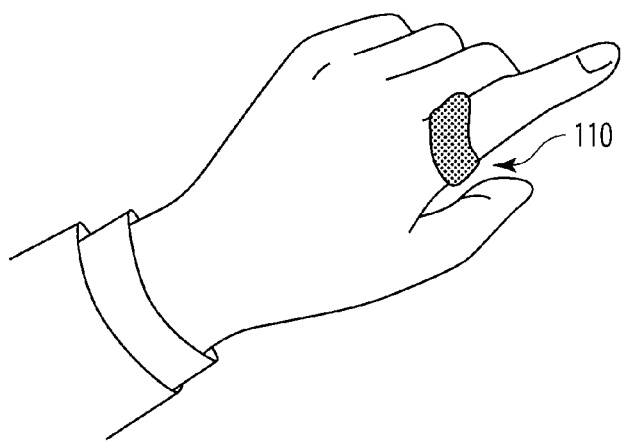
FIG. 2 is a diagram showing an example of the external configuration of a thermal sensation determining system shown in FIG. 1.

The thermal sensation determining system 110 is formed, for example, like a ring as shown in FIG. 2 and is installed at the base of the subject's finger. The temperature sensor 120 is provided on a surface of the system which is in close contact with the subject's skin. The skin temperature acquiring unit 101 continuously acquires the subject's skin temperature from the temperature sensor 120. The skin temperature acquiring unit 101 then inputs the skin temperature data acquired to the variation state determining unit 102 and the gradient detecting unit 103.

Now, description will be given of the technical significance of the measurement of the skin temperature of the base of the finger. Peripheral sites of the human body such as the base of the finger have a muscle layer and a large number of blood capillaries and arteriovenous communications which directly join arterioles and venulae. Precapillary sphincters exist around the periphery of the blood capillaries and open and close to adjust the amount of blood flowing into and out of the blood capillaries. The skin temperature is expected to vary within a short time depending on the varying amount of blood. Thus, the variation in skin temperature within a short time can be measured more easily at the peripheral sites than at a central site.

The thermal sensation determining system 110 may be installed, for example, at the tip of a finger or on the toe. Alternatively, the thermal sensation determining system 110 may be formed like a fake fingernail, instead of having the ring shape, so as to be installed on the nail of the hand or toe. That is, the thermal sensation determining system 110 has only to be able to utilize the skin temperature of the peripheral site having the arteriovenous communications. FIG. 2 does not limit the specific installation site or appearance of the thermal sensation determining system 110 according to the present embodiment. Furthermore, the thermal sensation determining system 110 and the temperature sensor 120 may be separated from each other. For example, the temperature sensor 120 may be formed like a ring, as previously described, and be installed on the subject's finger, while the thermal sensation determining system 110 may be formed like a wrist band and be installed on the subject's wrist. Additionally, a thermocouple or a thermistor may be used as the temperature sensor 120 in close contact with the skin, to measure the skin temperature. Thermography or a thermopile may be used to measure the skin temperature in a non-contact manner.

The variation state determining unit 102 traces back skin temperature data input by the skin temperature acquiring unit 101 through a preset first interval to determine whether the variation in skin temperature during the first interval is in a first state, a second state, or a third state which are set in the order of gradation; the variation in the first state being the most gradual. Specifically, the variation state determining unit 102 traces back through the first interval to detect the maximum value and the minimum value to calculate the difference between the values. If the difference is smaller than a preset temperature threshold, the variation state determining unit 102 determines that the first interval is in a first periodic variation state. On the other hand, if the difference is equal to or greater than the temperature threshold, the variation state determining unit 102 calculates a time duration equal to the difference between the time when the maximum skin temperature was detected and the time when the minimum skin temperature was detected. If the time duration is greater than a preset first time threshold, the variation state determining unit 102 determines that the first interval is in the first periodic variation state. If the time duration is equal to or smaller than the first time threshold and equal to or greater than a second time threshold smaller than the first time threshold, the variation state determining unit 102 determines that the first interval is in a second periodic variation state. If the time duration is smaller than the second time threshold, the variation state determining unit 102 determines that the first interval is in a third periodic variation state. Here, the first and second time thresholds are, for example, 120 seconds and 50 seconds, respectively.

The determination of the periodic variation state is not limited to the above-described technique. For example, the following technique may be used. The variation state determining unit 102 performs frequency analysis such as Fourier transformation on the variation in skin temperature in the first interval. If no peak is present in a preset frequency range, the variation state determining unit 102 determines this to be the first periodic variation state. If a peak is present within the preset frequency range and further within the range of frequencies lower than a predetermined frequency threshold, the variation state determining unit 102 determines this to be the second periodic variation state. If a peak is present within the preset frequency range and further within the range of frequencies equal to or higher than the frequency threshold, the variation state determining unit 102 determines this to be the third periodic variation state. Here, the frequency threshold is, for example, 0.01 [Hz].

The gradient detecting unit 103 traces back the skin temperature data input by the skin temperature acquiring unit 101 through a second interval, which is longer than the first interval. The gradient detecting unit 103 thus determines whether the temperature gradient of the skin temperature during the second interval is a first gradient that is greatest, a second gradient that is smaller than the first gradient, or a third gradient that is smaller than the second gradient. Specifically, if the temperature gradient is equal to or greater than a preset first gradient threshold, the gradient detecting unit 103 determines this to be the first gradient. If the temperature gradient is smaller than the first gradient threshold, and is equal to or greater than a preset second gradient threshold, which is smaller than the first gradient threshold, the gradient detecting unit 103 determines this to be the second gradient. If the temperature gradient is smaller than the second gradient threshold, the gradient detecting unit 103 determines this to be the third gradient. Here, for example, if the first gradient threshold is a positive quantity and the second gradient threshold is a negative quantity, the first temperature gradient is high on the right, whereas the third temperature gradient is low on the right.

The determination of the temperature gradient is not limited to the above-described technique. For example, the following technique may be used. If the variance in the skin temperature during the second interval is smaller than a preset variance threshold, the gradient detecting unit 103 determines this to be the second gradient. If the variance in the skin temperature during the second interval is equal to or greater than the variance threshold and the temperature gradient during the second interval is equal to or greater than a preset third gradient threshold, the gradient detecting unit 103 determines this to be the first gradient. If the variance in the skin temperature during the second interval is equal to or greater than the variance threshold and the temperature gradient is smaller than the third gradient threshold, the gradient detecting unit 103 determines this to be the third gradient. Here, the third gradient threshold is, for example, "0".

Now, description will be given of the relationship between the subject's thermal sensation and the periodic variation and the temperature gradient, with reference to the experiment results shown in FIG. 3. FIG. 3A shows the subject's thermal sensation felt by the subject when the environmental temperature is varied from 35° C. to 20° C. The ordinate axis shows numerical values from "3" to "−3", which indicate the thermal sensation. "3" corresponds to "hot", "2" corresponds to "a little hot", "1" corresponds to "warm". "0" corresponds to "comfortable", "−1" corresponds to "cool", "−2" corresponds to "a little cold", and "−3" corresponds to "cold".

FIG. 3B shows a variation in the skin temperature of a peripheral site of the subject's body corresponding to the temporal variation in thermal sensation shown in FIG. 3A. FIG. 3C shows the results of an operation of extracting intervals representative of "hot", "a little hot", "moderate", "a little cold", and "cold" from the graph shown in FIG. 3B, calculating the moving average of the data in these intervals for smoothing, performing differentiation of the moving average to remove trends, and further performing Fourier transformation of the differentiated moving average. In this case, provided that the periodic variation is determined on the basis of the results of the above-described frequency analysis, the "hot" interval and the "cold" interval belong to the first periodic variation state because the intervals have no peak within a preset frequency range (in this case, from 0 to 0.05 Hz). The "a little hot" interval and the "a little cold" interval have a peak within the range of frequencies lower than a predetermined frequency threshold (in this case, 0.01 Hz) and thus belong to the second periodic frequency state. The "moderate" interval has a peak within the range of frequencies equal to or greater than the frequency threshold and thus belongs to the third periodic variation state.

During the "cold" and "a little cold" intervals, the temperature gradient in FIG. 3B is low on the right. During the "hot", "a little hot", and "moderate" intervals, almost no temperature gradient can be identified (the temperature gradient is neither low nor high on the right). During the "hot" and "a light hot" intervals, the skin temperature does not vary significantly and remains mostly above 36° C. The results of other experiments (not shown) show that the gradient is high on the right during the "hot" and "a little hot" intervals. The present embodiment estimates the subject's thermal sensation on the basis of the relationship between the thermal sensation and the periodic variation state, temperature gradient, and absolute value of the subject's peripheral skin temperature.

The thermal sensation determining unit 104 determines a thermal sensation determination value Xnew using the most recent thermal sensation determination value Xold, the current peripheral skin temperature (or the average value of the skin temperatures acquired in a preset previous interval) Tp acquired by the skin temperature acquiring unit 101, thresholds Tt1, Tt2, and Tt3 for the peripheral skin temperature Tp, the periodic variation state determined by the variation state determining unit 102, the temperature gradient determined by the gradient detecting unit 103, and a counting variable N, a threshold Nt for the variable N, an adjustment value α for a thermal sensation determination value, and a flag FLAG0. Specifically, the thermal sensation determining unit 104 operates in accordance with one of the flows shown in FIGS. 4 to 12, which is determined by the periodic variation state and temperature gradient, to output the new thermal sensation determination value Xnew.

If the periodic variation is in the first state and the temperature gradient is the first gradient, the subject is expected to feel "hot" on the basis of the above-described experiment results. The thermal sensation determining unit 104 thus operates as shown in FIG. 4. First, the thermal sensation determining unit 104 reads the most recent thermal sensation determination value Xold from the storage unit 112 via the control unit 114 to determine whether or not the value Xold is smaller than "3" (step S201). If the most recent thermal sensation determination value Xold is smaller than "3", the thermal sensation determination unit 104 adds the adjustment value α to the thermal sensation determination value Xold to output the resultant value as the current thermal sensation determination value Xnew (step S202). In this case, the adjustment value α may be a fixed value, for example, "1" or a variable value determined on the basis of a certain function. On the other hand, if the most recent thermal sensation determination value Xold is at least "3", the thermal sensation determining unit 104 directly outputs the thermal sensation determination value Xold as the current thermal sensation determination value Xnew (step S203). The maximum value of Xnew is preferably "3".

If the periodic variation is in the first state and the temperature gradient is the second gradient, the subject is expected to feel "cold" or "hot" on the basis of the above-described experiment results. The thermal sensation determining unit 104 thus operates as shown in FIG. 5. First, the thermal sensation determining unit 104 determines whether or not the skin temperature Tp is higher than the threshold Tt1 (step S211). Here, the threshold Tt1 is, for example, 36° C. on the basis of the above-described experiment results. That is, in step S211, the thermal sensation determining unit 104 roughly determines whether or not the subject feels "hot". If the skin temperature Tp is higher than the threshold Tt1, the thermal sensation determining unit 104 reads the most recent thermal sensation determination value Xold from the storage unit 112 via the control unit 114 to determine whether or not the value Xold is smaller than "3" (step S212). If the most recent thermal sensation determination value Xold is smaller than "3", the thermal sensation determination unit 104 adds the adjustment value α to the thermal sensation determination value Xold to output the resultant value as the current thermal sensation determination value Xnew (step S213). On the other hand, if the most recent thermal sensation determination value is at least "3", the thermal sensation determining unit 104 directly outputs the thermal sensation determination value Xold as the current thermal sensation determination value Xnew (step S214). The maximum value of Xnew is preferably "3".

If the skin temperature Tp is equal to or lower than the threshold Tt1 (step S211), the thermal sensation determining unit 104 reads the most recent thermal sensation determination value Xold from the storage unit 112 via the control unit 114 to determine whether or not the value Xold is greater than "−3" (step S215). If the most recent thermal sensation determination value Xold is greater than "−3", the thermal sensation determination unit 104 subtracts the adjustment value α from the thermal sensation determination value Xold to output the resultant value as the current thermal sensation determination value Xnew (step S216). On the other hand, if the most recent thermal sensation determination value Xold is at most "−3", the thermal sensation determining unit 104 directly outputs the thermal sensation determination value Xold as the current thermal sensation determination value Xnew (step S217). The minimum value of Xnew is preferably "−3".

Figure 6:
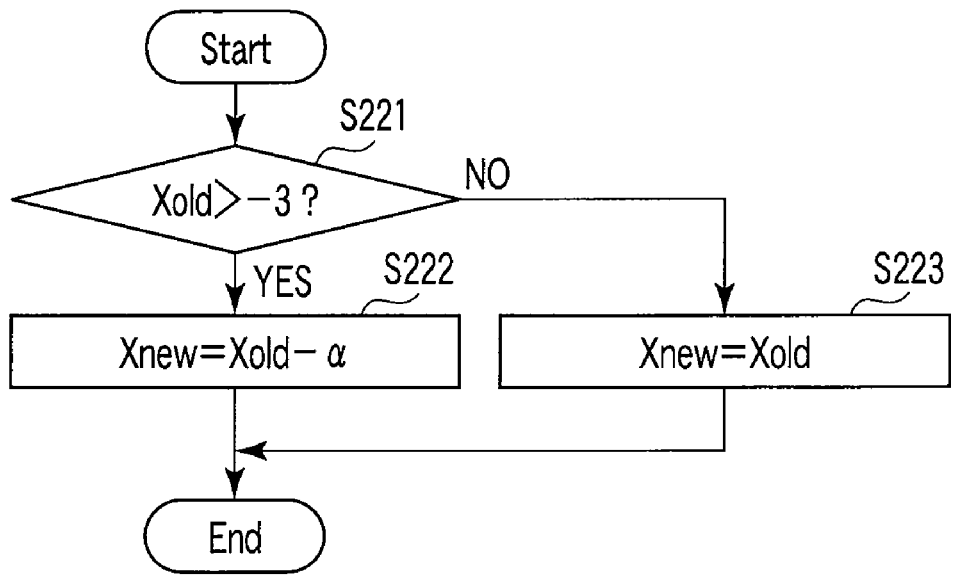
FIG. 6 is a flowchart showing a determining operation performed by the thermal sensation determining unit shown in FIG. 1 when the periodic variation is in the first state and the temperature gradient is a third gradient.

If the periodic variation is in the first state and the temperature gradient is the third gradient, the subject is expected to feel "cold" on the basis of the above-described experiment results. The thermal sensation determining unit 104 thus operates as shown in FIG. 6. First, the thermal sensation determining unit 104 reads the most recent thermal sensation determination value Xold from the storage unit 112 via the control unit 114 to determine whether or not the value Xold is greater than "−3" (step S221). If the most recent thermal sensation determination value Xold is greater than "−3", the thermal sensation determination unit 104 subtracts the adjustment value α from the thermal sensation determination value Xold to output the resultant value as the current thermal sensation determination value Xnew (step S222). On the other hand, if the most recent thermal sensation determination value Xold is at most "−3", the thermal sensation determining unit 104 directly outputs the thermal sensation determination value Xold as the current thermal sensation determination value Xnew (step S223). The minimum value of Xnew is preferably "−3".

Figure 7:
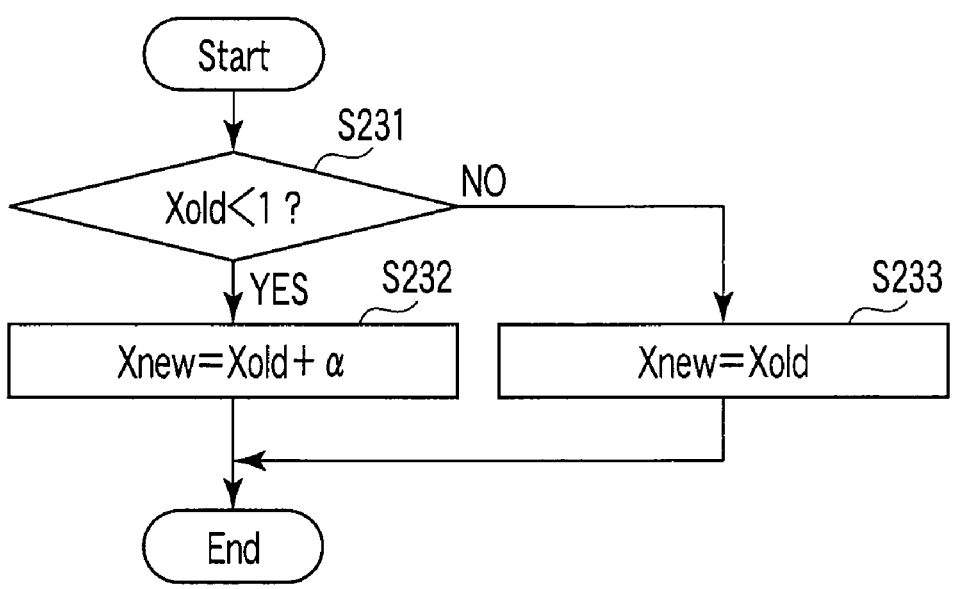
FIG. 7 is a flowchart showing a determining operation performed by the thermal sensation determining unit shown in FIG. 1 when the periodic variation is in a second state and the temperature gradient is the first gradient.

If the periodic variation is in the second state and the temperature gradient is the first gradient, the subject is expected to feel somewhat "hot" on the basis of the above-described experiment results. The thermal sensation determining unit 104 thus operates as shown in FIG. 7. First, the thermal sensation determining unit 104 reads the most recent thermal sensation determination value Xold from the storage unit 112 via the control unit 114 to determine whether or not the value Xold is smaller than "1" (step S231). If the most recent thermal sensation determination value Xold is smaller than "1", the thermal sensation determination unit 104 adds the adjustment value α to the thermal sensation determination value Xold to output the resultant value as the current thermal sensation determination value Xnew (step S232). On the other hand, if the most recent thermal sensation determination value Xold is at least "1", the thermal sensation determining unit 104 directly outputs the thermal sensation determination value Xold as the current thermal sensation determination value Xnew (step S233).

Figure 8:
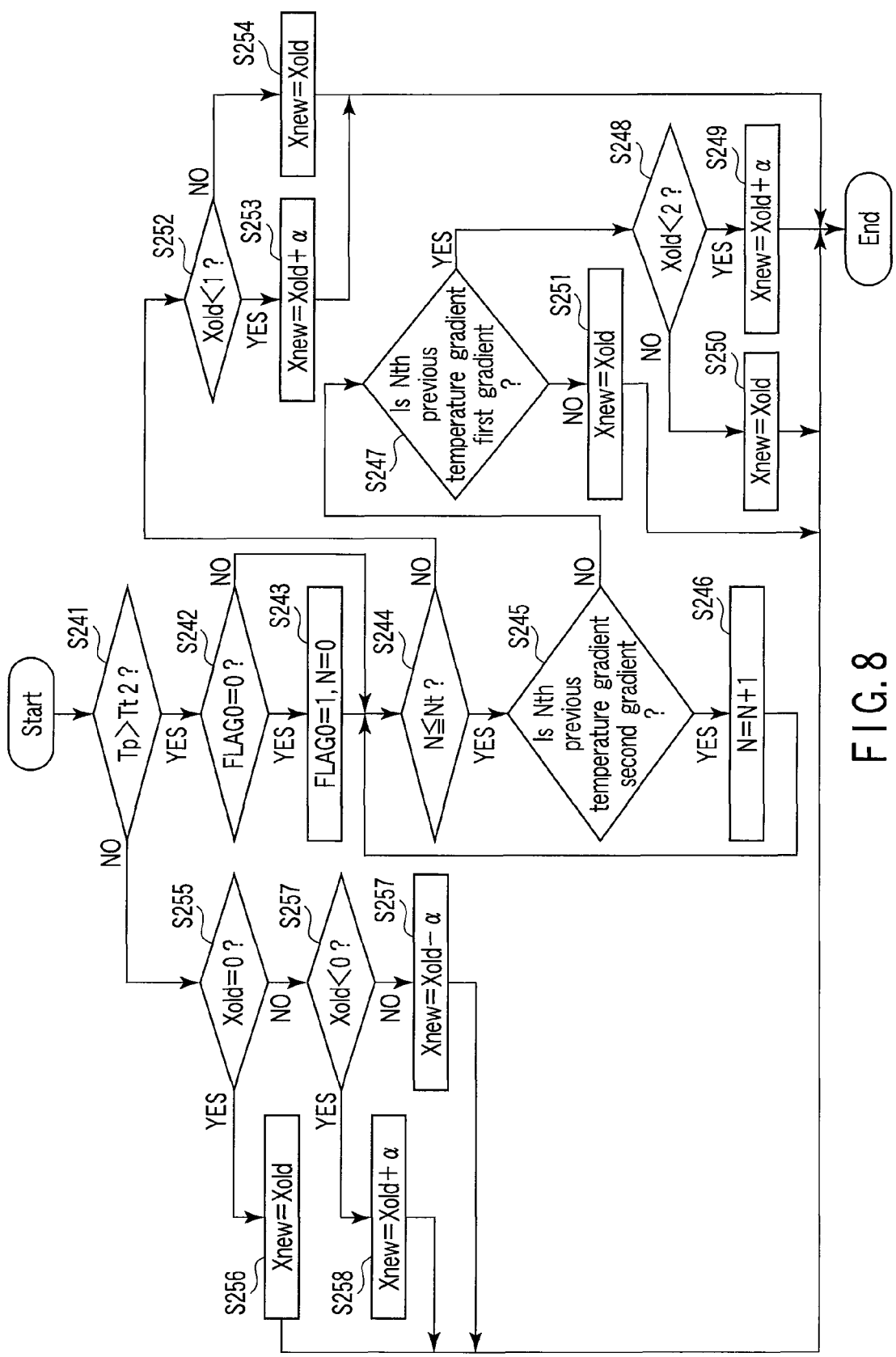
FIG. 8 is a flowchart showing a determining operation performed by the thermal sensation determining unit shown in FIG. 1 when the periodic variation is in the second state and the temperature gradient is the second gradient.

If the periodic variation is in the second state and the temperature gradient is the second gradient, it is difficult to predict the subject's thermal sensation on the basis of the above-described experiment results. The thermal sensation determining unit 104 thus operates as shown in FIG. 8. First, the thermal sensation determining unit 104 determines whether or not the skin temperature Tp is higher than the threshold Tt2 (for example, 36° C.) (step S241). If the skin temperature Tp is higher than the threshold Tt2, the thermal sensation determining unit 104 determines whether or not the flag FLAG0 is "0" (step S242). Here, the flag FLAG0 indicates whether or not a thermal sensation determining process performed to obtain the most recent thermal sensation determination value Xold is the process shown in FIG. 8. The flag FLAG0 is saved as long as the thermal sensation determining unit 102 continuously performs the process shown in FIG. 8. However, the flag FLAG0 is set to "0" when the thermal sensation determining unit 104 performs a process different from that shown in FIG. 8. If the flag FLAG0 is "0", the thermal sensation determining unit 104 substitutes "1" into the flag FLAG0 and "0" into the counting variable N, the process proceeds to step S244 (step S243). On the other hand, if the flag FLAG0 is "0", the process proceeds to step S244 without performing step S243.

In step S244, the thermal sensation determining unit 104 determines whether or not the counting variable N is equal to the threshold Nt. Here, the threshold Nt is, for example, the number of times that the gradient detecting unit 103 has determined the temperature gradient. If the counting variable N is equal to or smaller than the threshold Nt, the thermal sensation determining unit 104 determines whether or not the Nth previous determination of the temperature gradient made by the gradient detecting unit 103 corresponds to the second gradient (step S245). If the Nth previous determination of the temperature gradient made by the gradient detecting unit 103 corresponds to the second gradient, the thermal sensation determining unit 104 increments the counting variable N by one. The process then returns to step S244 (step S246). On the other hand, if the Nth previous determination of the temperature gradient made by the gradient detecting unit 103 does not correspond to the second gradient, the thermal sensation determining unit 104 determines whether or not the determination corresponds to the first gradient (step S247). If the Nth previous determination of the temperature gradient made by the gradient detecting unit 103 corresponds to the first gradient, the thermal sensation determining unit 104 reads the most recent thermal sensation determination value Xold from the storage unit 112 via the control unit 114 to determine whether or not the value Xold is smaller than "2" (step S248). If the most recent thermal sensation determination value Xold is smaller than "2", the thermal sensation determining unit 104 adds the adjustment value α to the thermal sensation determination value Xold to output the resultant value as the current thermal sensation determination value Xnew (step S249). On the other hand, if the most recent thermal sensation determination value is at least "2", the thermal sensation determining unit 104 directly outputs the thermal sensation determination value Xold as the current thermal sensation determination value Xnew (step S250).

If the Nth previous determination of the temperature gradient made by the gradient detecting unit 104 corresponds to the third gradient (step S247), the thermal sensation determining unit 104 directly outputs the most recent thermal sensation determination value Xold as the current thermal sensation determination value Xnew (step S251).

If the counting variable N is greater than the threshold Nt (step S244), the thermal sensation determining unit 104 reads the most recent thermal sensation determination value Xold from the storage unit 112 via the control unit 114 to determine whether or not the value Xold is smaller than "1" (step S252). If the most recent thermal sensation determination value Xold is smaller than "1", the thermal sensation determination unit 104 adds the adjustment value α to the thermal sensation determination value Xold to output the resultant value as the current thermal sensation determination value Xnew (step S253). On the other hand, if the most recent thermal sensation determination value Xold is at least "1", the thermal sensation determining unit 104 directly outputs the thermal sensation determination value Xold as the current thermal sensation determination value Xnew (step S254).

If the skin temperature Tp is equal to or lower than the threshold Tt2 (step S241), the thermal sensation determining unit 104 reads the most recent thermal sensation determination value Xold from the storage unit 112 via the control unit 114 to determine whether or not the value Xold is "0" (step S255). If the most recent thermal sensation determination value Xold is "0", the thermal sensation determination unit 104 directly outputs the thermal sensation determination value Xold (="0") as the current thermal sensation determination value Xnew (step S256). On the other hand, if the most recent thermal sensation determination value Xold is other than "0", the thermal sensation determining unit 104 determines whether or not the most recent thermal sensation determination value Xold is smaller than "0" (step S257). If the most recent thermal sensation determination value Xold is smaller than "0", the thermal sensation determining unit 104 adds the adjustment value α to the thermal sensation determination value Xold to output the resultant value as the current thermal sensation determination value Xnew (step S258). On the other hand, if the most recent thermal sensation determination value Xold is greater than "0", the thermal sensation determining unit 104 subtracts the adjustment value α from the thermal sensation determination value Xold to output the resultant value as the current thermal sensation determination value Xnew (step S259).

Figure 9:
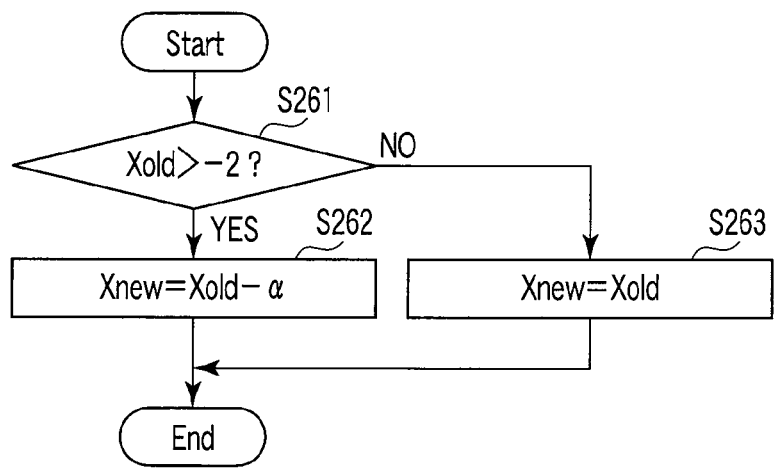
FIG. 9 is a flowchart showing a determining operation performed by the thermal sensation determining unit shown in FIG. 1 when the periodic variation is in the second state and the temperature gradient is the third gradient.

If the periodic variation is in the second state and the temperature gradient is the third gradient, the subject is expected to feel somewhat "cold" on the basis of the above-described experiment results. The thermal sensation determining unit 104 thus operates as shown in FIG. 9. First, the thermal sensation determining unit 104 reads the most recent thermal sensation determination value Xold from the storage unit 112 via the control unit 114 to determine whether or not the value Xold is greater than "−2" (step S261). If the most recent thermal sensation determination value Xold is greater than "−2", the thermal sensation determination unit 104 subtracts the adjustment value α from the thermal sensation determination value Xold to output the resultant value as the current thermal sensation determination value Xnew (step S263). On the other hand, if the most recent thermal sensation determination value Xold is at most "−2", the thermal sensation determining unit 104 directly outputs the thermal sensation determination value Xold as the current thermal sensation determination value Xnew.

Figure 10:
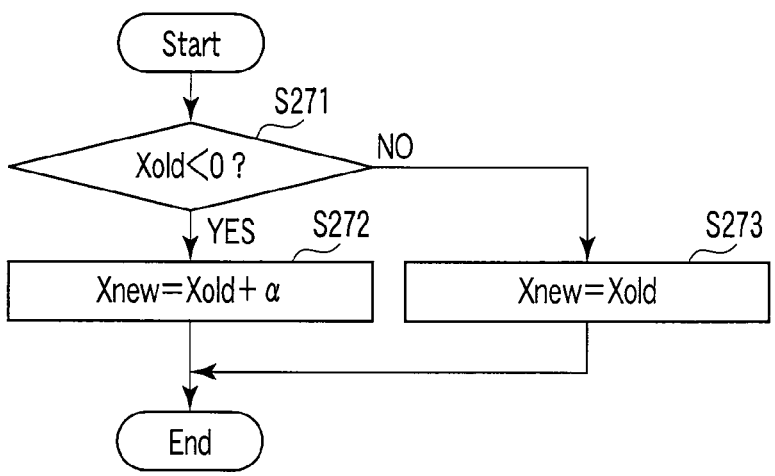
FIG. 10 is a flowchart showing a determining operation performed by the thermal sensation determining unit shown in FIG. 1 when the periodic variation is in a third state and the temperature gradient is the first gradient.

If the periodic variation is in the third state and the temperature gradient is the first gradient, the subject is expected to feel that the temperature is "moderate" or to feel somewhat "hot" on the basis of the above-described experiment results. The thermal sensation determining unit 104 thus operates as shown in FIG. 10. First, the thermal sensation determining unit 104 reads the most recent thermal sensation determination value Xold from the storage unit 112 via the control unit 114 to determine whether or not the value Xold is smaller than "0" (step S271). If the most recent thermal sensation determination value Xold is smaller than "0", the thermal sensation determination unit 104 adds the adjustment value α to the thermal sensation determination value Xold to output the resultant value as the current thermal sensation determination value Xnew (step S272). On the other hand, if the most recent thermal sensation determination value is at least "0", the thermal sensation determining unit 104 directly outputs the thermal sensation determination value Xold as the current thermal sensation determination value Xnew (step S273).

Figure 11:
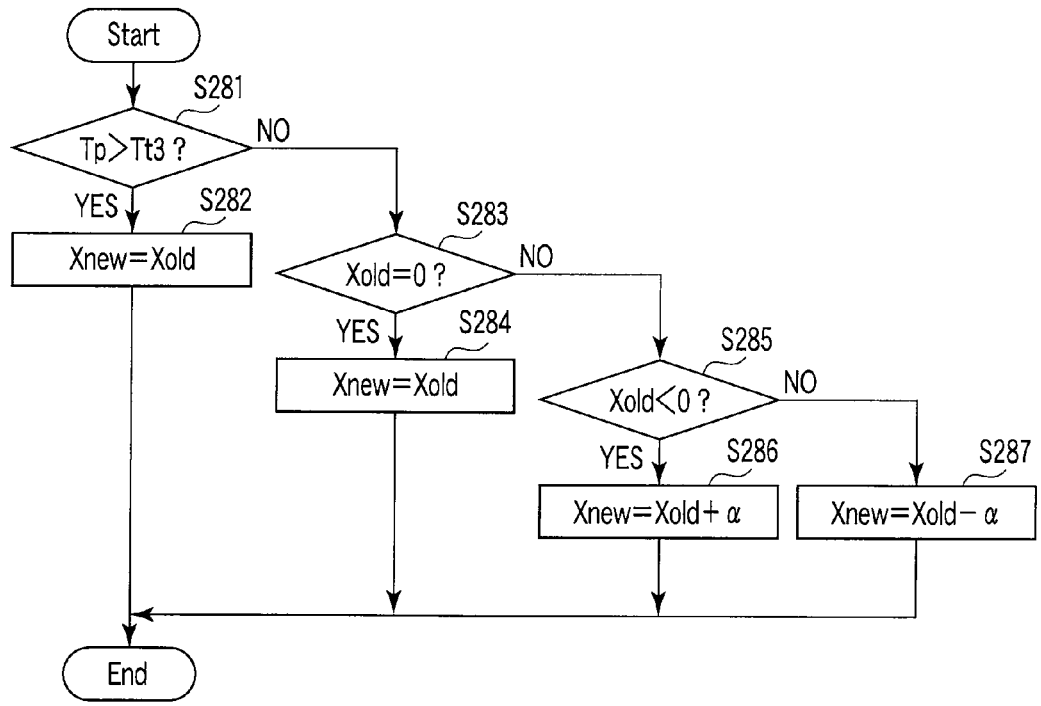
FIG. 11 is a flowchart showing a determining operation performed by the thermal sensation determining unit shown in FIG. 1 when the periodic variation is in the third state and the temperature gradient is the second gradient.

If the periodic variation is in the third state and the temperature gradient is the second gradient, the subject is expected to feel that the temperature is "moderate" on the basis of the above-described experiment results. The thermal sensation determining unit 104 thus operates as shown in FIG. 11. First, the thermal sensation determining unit 104 determines whether or not the skin temperature Tp is higher than the threshold Tt3 (step S281). Here, the threshold Tt3 is, for example, 36° C. on the basis of the above-described experiment results. If the skin temperature Tp is higher than the threshold Tt3, the thermal sensation determining unit 104 reads the most recent thermal sensation determination value Xold from the storage unit 112 via the control unit 114 to directly output the most recent thermal sensation determination value Xold as the current thermal sensation determination value Xnew (step S282). On the other hand, if the skin temperature Tp is equal to or lower than the threshold Tt3, the thermal sensation determining unit 104 determines whether or not the most recent thermal sensation determination value Xold is "0" (step S283). If the most recent thermal sensation determination value Xold is "0", the thermal sensation determining unit 104 directly outputs the thermal sensation determination value Xold as the current thermal sensation determination value Xnew (step S284). On the other hand, if the most recent thermal sensation determination value Xold is other than "0", the thermal sensation determining unit 104 determines whether or not the most recent thermal sensation determination value Xold is smaller than "0" (step S285). If the most recent thermal sensation determination value Xold is smaller than "0", the thermal sensation determining unit 104 adds the adjustment value α to the thermal sensation determination value Xold to output the resultant value as the current thermal sensation determination value Xnew (step S286). On the other hand, if the most recent thermal sensation determination value Xold is greater than "0", the thermal sensation determining unit 104 subtracts the adjustment value α from the thermal sensation determination value Xold to output the resultant value as the current thermal sensation determination value Xnew (step S287).

Figure 12:
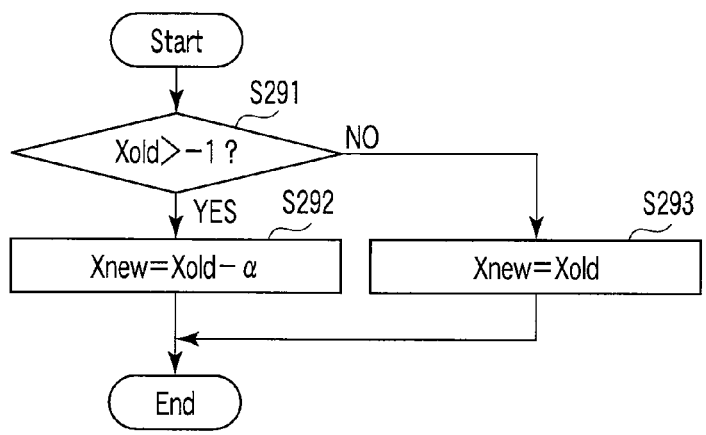
FIG. 12 is a flowchart showing a determining operation performed by the thermal sensation determining unit shown in FIG. 1 when the periodic variation is in the third state and the temperature gradient is the third gradient.

If the periodic variation is in the third state and the temperature gradient is the third gradient, the subject is expected to feel that the temperature is "moderate" or to feel somewhat "cold" on the basis of the above-described experiment results. The thermal sensation determining unit 104 thus operates as shown in FIG. 12. First, the thermal sensation determining unit 104 reads the most recent thermal sensation determination value Xold from the storage unit 112 via the control unit 114 to determine whether or not the value Xold is greater than "−1" (step S291). If the most recent thermal sensation determination value Xold is greater than "−1", the thermal sensation determination unit 104 subtracts the adjustment value α from the thermal sensation determination value Xold to output the resultant value as the current thermal sensation determination value Xnew (step S292). On the other hand, if the most recent thermal sensation determination value is at most "−1", the thermal sensation determining unit 104 directly outputs the thermal sensation determination value Xold as the current thermal sensation determination value Xnew (step S293).

The input unit 111 receives an instruction from the subject ordering the thermal sensation determining system 110 to start or end the thermal sensation determination. When the instruction ordering the thermal sensation determining system 110 to start the thermal sensation determination is input to the input unit 111, the control unit 114 allows the thermal sensation determining apparatus 100 to start operation. When the instruction ordering the thermal sensation determining system 110 to end the thermal sensation determination is input to the input unit 111, the control unit 114 allows the thermal sensation determining apparatus 100 to end operation.

The following are recorded in the storage unit 112: the skin temperature data acquired by the skin temperature acquiring unit 101, the periodic variation state determined by the periodic variation determining unit 102, the temperature gradient detected by the gradient detecting unit 103, the thermal sensation determination value obtained by the thermal sensation determining unit 104, and various other parameters required for the determination.

The power supply unit 113 supplies power to the whole thermal sensation determining system 110. The control unit 114 controls the whole thermal sensation determining system 110. The control unit 114 controls, for example, process requests sent to the appropriate units and the flow of data.

As described above, the thermal sensation determining apparatus according to the present embodiment determines the thermal sensation step by step on the basis of the absolute value of the peripheral skin temperature, periodic variation, and temperature gradient of the peripheral skin temperature. Therefore, the thermal sensation determining apparatus according to the present embodiment allows the thermal sensation to be easily determined in detail.

Second Embodiment

As shown in FIG. 13, a thermal sensation determining apparatus 300 according to a second embodiment of the thermal sensation determining apparatus 100 shown in FIG. 1 and further having an environmental temperature acquiring unit 305 and a determination value correcting unit 306. The thermal sensation determining apparatus 300 is incorporated in a thermal sensation determining system 310. A temperature sensor 321 measuring the environmental temperature is connected to the thermal sensation determining system 310. In FIG. 13, the same components as those shown in FIG. 1 are denoted by the same reference numerals and will not be described in detail, and only the differences will be mainly described.

The environmental temperature acquiring unit 305 continuously acquires the environmental temperature around the subject from the temperature sensor 321. Now, the relationship between the environmental temperature and the thermal sensation will be described. In certain experiments, when the environmental temperature varied as shown in FIG. 14A, the subject felt such thermal sensation as shown in FIG. 14B. As shown in FIG. 14A, during a time of 25 [min] to a time of 45 [min], the environmental temperature is maintained at 25 degrees, and the subject's peripheral skin temperature remains lower than the environmental temperature. In the meantime, the subject's thermal sensation continues to be degraded as shown in FIG. 14B. On the other hand, during a time of 50 [min] to a time of 70 [min], the environmental temperature is maintained at about 28 degrees. After a time of 60 [min], the subject's peripheral skin temperature remains higher than the environmental temperature. However, in contrast to the above-described example, although the subject's peripheral skin temperature remains higher than the environmental temperature, the thermal sensation varies around the comfortable ("0") level. The results of the experiments indicate that when the subject's peripheral skin temperature remains lower than the environmental temperature, the subject's thermal sensation tends to be degraded. The thermal sensation determination value obtained by the thermal sensation determining unit 104 thus needs to be corrected.

Figure 15:
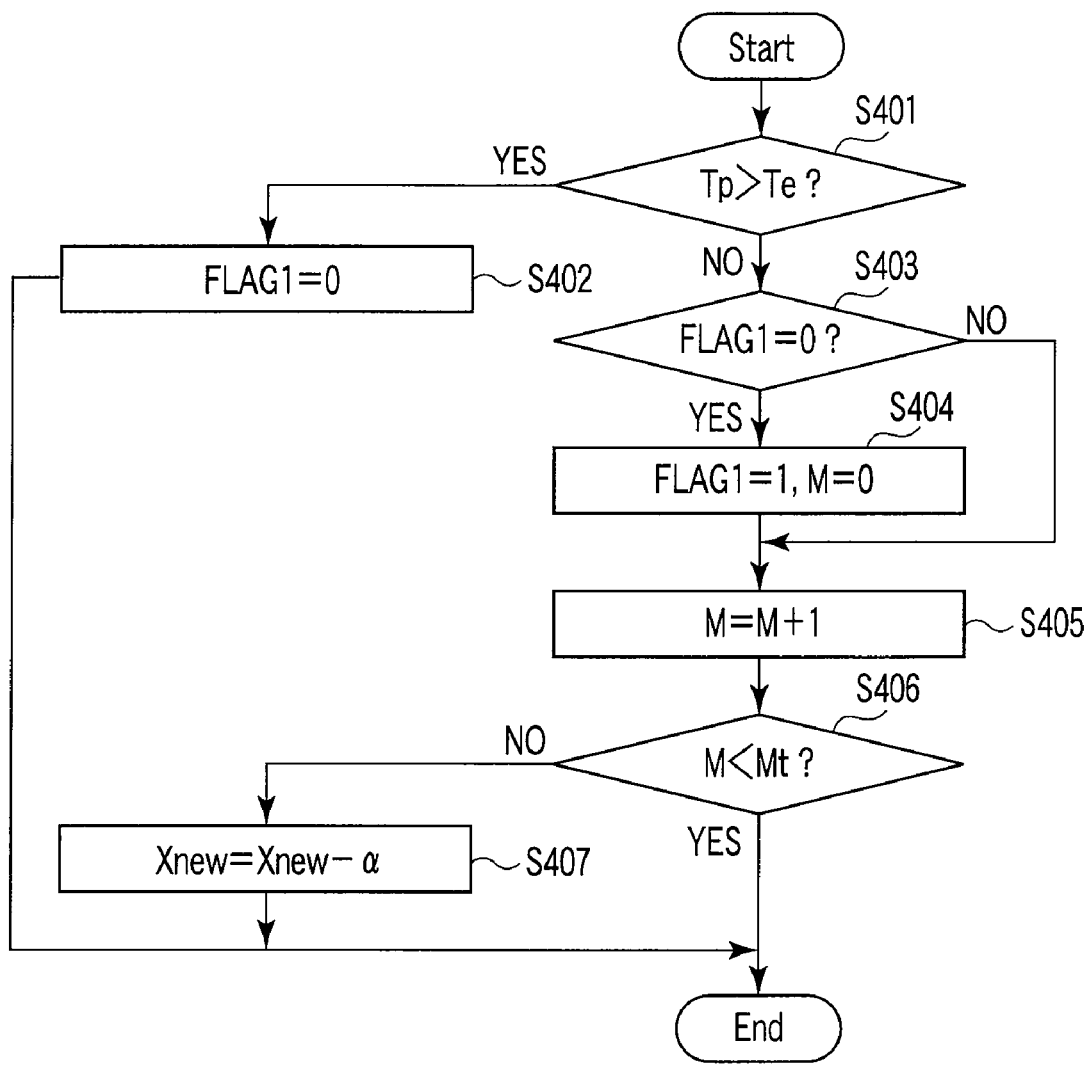
FIG. 15 is a flowchart showing a correcting operation of a determination value correcting unit shown in FIG. 13.

The determination value correcting unit 306 corrects the thermal sensation determination value Xnew using the thermal sensation determination value Xnew determined by the thermal sensation determining unit 104, the current peripheral skin temperature (or the average value of the skin temperatures acquired in a preset previous interval) Tp acquired by the skin temperature acquiring unit 101, and a variable M required to count the number of times that the peripheral skin temperature Tp continues to be lower than the environmental temperature Te, a threshold Mt for the variable M, the adjustment value α for the thermal sensation determination value Xnew, and a flag FLAG1 indicating whether or not the peripheral skin temperature Tp was lower than the environmental temperature Te during the most recent correcting process. Now, a correcting process performed by the determination value correcting unit 306 will be described with reference to a flowchart shown in FIG. 15.

First, the determination value correcting unit 306 determines whether or not the peripheral skin temperature Tp is higher than the environmental temperature Te (step S401). If the peripheral skin temperature Tp is higher than the environmental temperature Te, the thermal sensation determination value Xnew need not be corrected. The determination value correcting unit 306 substitutes "0" into the flag FLAG1 and the process is ended. On the other hand, if the peripheral skin temperature Tp is equal to or lower than the environmental temperature Te, the determination value correcting unit 306 determines whether or not the flag FLAG1 is "0" (step S403). If the flag FLAG1 is "0", the determination value correcting unit 306 substitutes "1" into the flag FLAG1 and "0" into the variable M for resetting. The process proceeds to step S405 (step S404). On the other hand, if the flag FLAG1 is "1", step S404 is omitted and the process proceeds to step S405 (step S403).

In step S405, the determination value correcting unit 306 increments the variable M by "1". The determination value correcting unit 306 then determines whether or not the variable M is smaller than the threshold Mt (step S406). Here, the threshold Mt is a threshold required for the determination value correcting unit 306 to correct the thermal sensation determination value Xnew. Accordingly, the threshold Mt may vary accordingly, depending on, for example, the period at which the thermal sensation determining unit 104 makes the thermal sensation determination. If the variable M is smaller than the threshold Mt, the determination value correcting unit 306 ends the process without performing any correction. On the other hand, if the variable M is equal to or greater than the threshold Mt, the determination value correcting unit 306 subtracts the adjustment value α from the thermal sensation determination value Xnew to obtain the corrected thermal sensation determination value Xnew (step S407).

As described above, the present embodiment corrects the thermal sensation determination value so that if the subject's peripheral skin temperature continues to be lower than the environmental temperature, the thermal sensation determination value is reduced. The present embodiment can thus eliminate the difference between the thermal sensation felt by the subject when the peripheral skin temperature continues to be lower than the environmental temperature and the thermal sensation determined by the thermal sensation determining apparatus.

Third Embodiment

Figure 16:
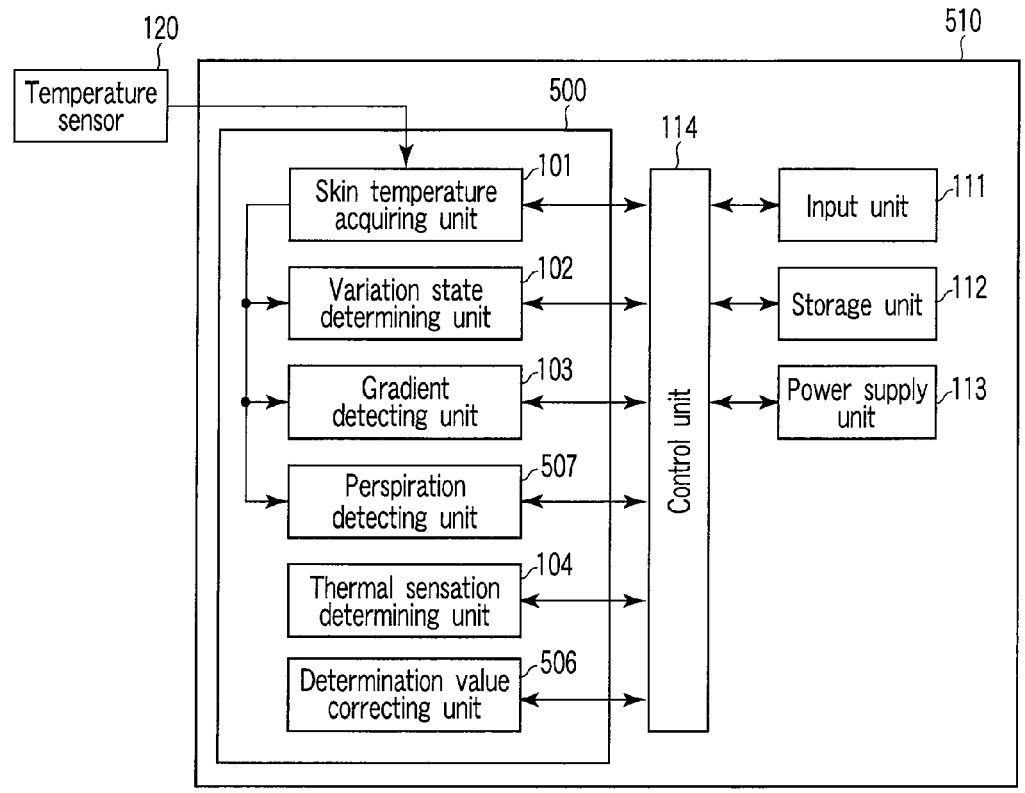
FIG. 16 is a block diagram showing a thermal sensation determining apparatus according to a third embodiment.

As shown in FIG. 16, a thermal sensation determining apparatus 500 according to a third embodiment of the thermal sensation determining apparatus 100 shown in FIG. 1 and further having a determination value correcting unit 506 and a perspiration detecting unit 507. The thermal sensation determining apparatus 500 is incorporated into a thermal sensation determining system 510. In FIG. 16, the same components as those shown in FIG. 1 are denoted by the same reference numerals and will not be described in detail. Differences from FIG. 1 will be mainly described.

Figure 17A:
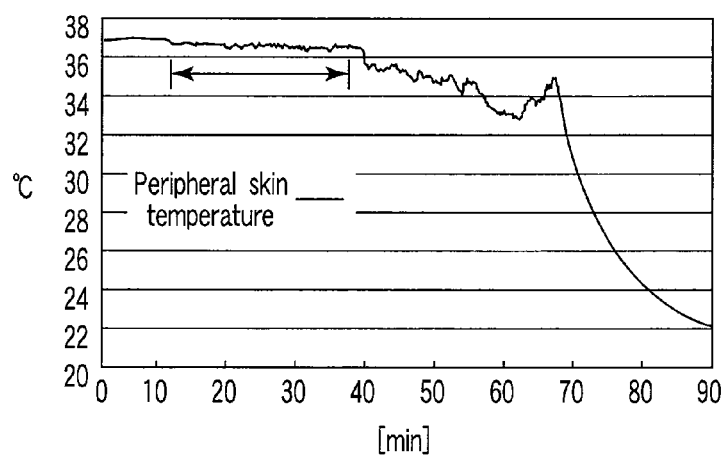
FIG. 17A is a graph showing a variation in the subject's peripheral skin temperature.
Figure 17B:
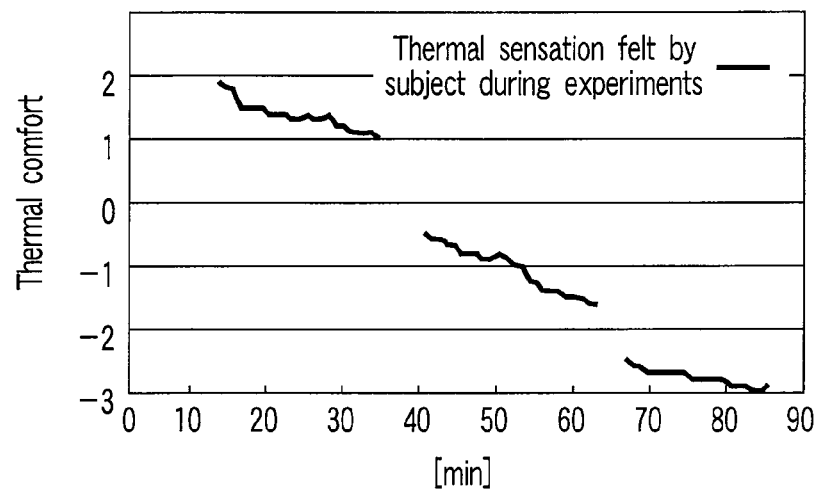
FIG. 17B is a graph corresponding to FIG. 17A and showing the subject's thermal sensation.
Figure 17C:
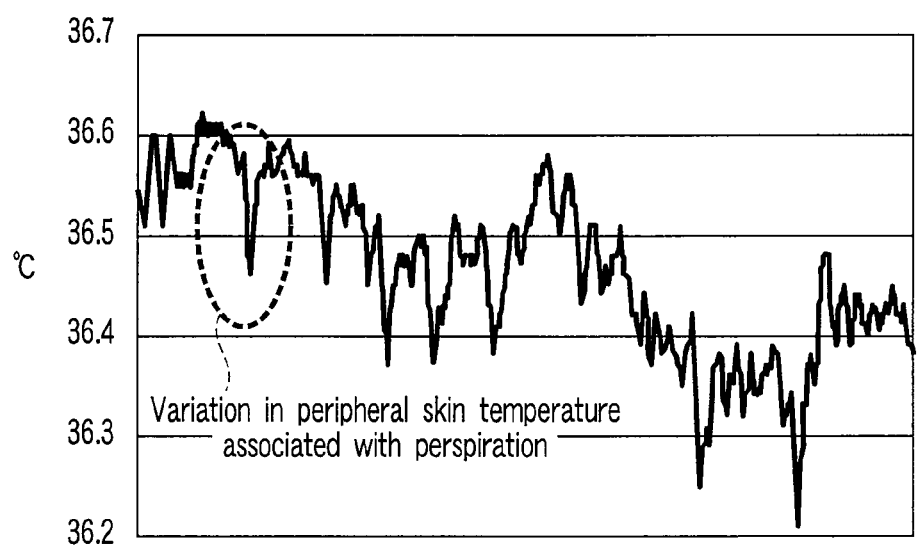
FIG. 17C is an enlarged graph showing a region shown in FIG. 17A by an arrow.

First, the relationship between perspiration and the thermal sensation will be described. In certain experiments, when the subject's peripheral skin temperature varied as shown in FIG. 17A, the subject felt such thermal sensation as shown in FIG. 17B. The waveform in an interval (the interval during which the subject's thermal sensation is "1" to "2", that is, "warm" to "a little hot"), specified by an arrow in FIG. 17A, was enlarged to obtain a waveform shown in FIG. 17C. FIG. 17C shows a fluctuation in skin temperature, particularly a sharp, downward projecting waveform. The intervals during which the subject felt the other levels of the thermal sensation were verified. Such a sharp, downward projecting waveform (fluctuation) was particularly often observed during the intervals during which the subject felt the "warm" to "a little hot" thermal sensation. Therefore, a temporary decrease in the subject's peripheral skin temperature is expected to result from perspiration. The reason why such a fluctuation is not often observed in the vicinity of the interval during which the subject felt the "hot" thermal sensation is that radiation resulting from perspiration relatively insignificantly affects the surrounding environmental temperature.

The perspiration detecting unit 507 is an adaptive filter that detects the above-described waveform in skin temperature data acquired by the skin temperature acquiring unit 101 on the basis of the fluctuation in the waveform of the skin temperature associated with perspiration. When the perspiration detecting unit 507 detects the subject's perspiration, the determination value correcting unit 506 corrects the thermal sensation determination value Xnew obtained by the thermal sensation determining unit 104. The specific correction method is not particularly limited. For example, a flag FLAG2 indicating whether or not perspiration has occurred is provided. When the perspiration detecting unit 507 detects the subject's perspiration, "1" is substituted into the flag FLAG2. When the flag FLAG2 is "1", the determination value correcting unit 506 substitutes "0" into the flag FLAG2 for resetting. Next, if the thermal sensation determination value Xnew obtained by the thermal sensation determining unit 104 is smaller than "1", the determination value correcting unit 506 adds the adjustment value α to the thermal sensation determination value Xnew for correction.

As described above, the present embodiment corrects the thermal sensation determination value if the subject's perspiration is detected. The present embodiment can thus eliminate the difference between the thermal sensation actually felt by the subject in such a relatively hot environment as involves the detection of the subject's perspiration and the thermal sensation determined by the thermal sensation determining apparatus.

Fourth Embodiment

As shown in FIG. 18, an air-conditioning control system 610 according to a fourth embodiment of the present invention corresponds to the thermal sensation determining system 110 shown in FIG. 1 and further has an controller 615 to allow air-conditioning control to be performed on an air-conditioning apparatus 630. In FIG. 18, the same components as those shown in FIG. 1 are denoted by the same reference numerals and will not be described in detail. Differences from FIG. 1 will be mainly described.

Figure 19:
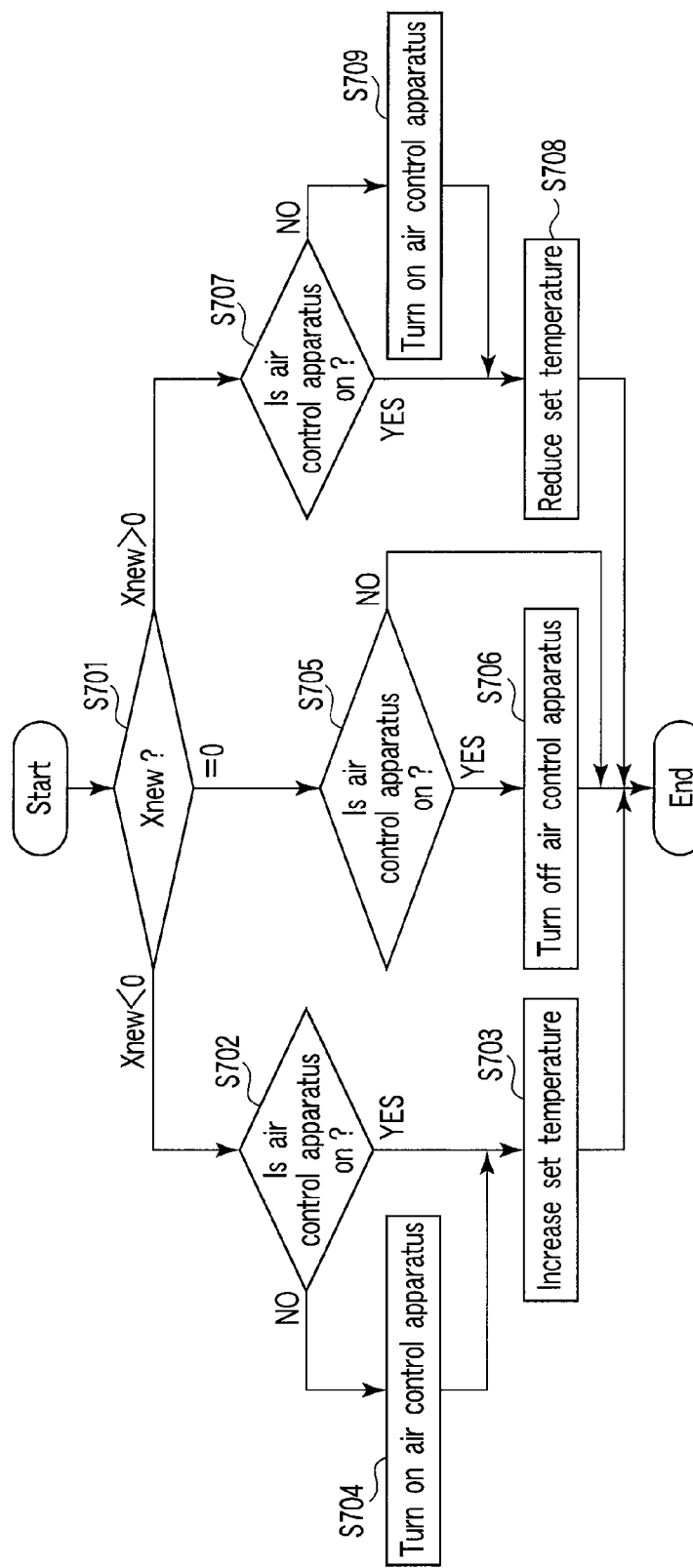
FIG. 19 is a flowchart showing an air-conditioning control operation of the air-conditioning control system shown in FIG. 18.

The controller 615 uses the thermal sensation determination value Xnew obtained by the thermal sensation determining unit 104 to control the operation of the air-conditioning apparatus 630. With reference to a flowchart shown in FIG. 19, description will be given below of an example of an operation performed by the air-conditioning control system 610 to control the turning-on and -off of the air-conditioning apparatus 630 as well as a set temperature for the air-conditioning apparatus 630.

First, the controller 615 checks the thermal sensation determination value Xnew (step S701). If the thermal sensation determination value Xnew is smaller than "0", the subject feels somewhat cold. The process then proceeds to step S702 in order to make the subject's thermal sensation closer to the level of the moderate temperature. In step S702, the controller 615 determines whether or not the air-conditioning apparatus 630 is on. If the air-conditioning apparatus 630 is off, the controller 615 turns on the air-conditioning apparatus 630, and the process proceeds to step S703 (step S704). On the other hand, if the air-conditioning apparatus 630 is on, and the process proceeds to step S703 with step S704 omitted. In step S703, the controller 615 increases the set temperature for the air-conditioning apparatus 630.

If the thermal sensation determination value Xnew is "0", the subject feels that the temperature is moderate. The process then proceeds to step S705 in order to maintain this environment. In step S705, the controller 615 determines whether or not the air-conditioning apparatus 630 is on. If the air-conditioning apparatus 630 is on, the controller 615 turns off the air-conditioning apparatus 630 (step S706). On the other hand, if the air-conditioning apparatus 630 is off, the controller 615 does nothing.

If the thermal sensation determination value Xnew is larger than "0", the subject feels somewhat hot. The process thus proceeds to step S707 in order to make the subject's thermal sensation closer to the level of the moderate temperature. In step S707, the controller 615 determines whether or not the air-conditioning apparatus 630 is on. If the air-conditioning apparatus 630 is off, the controller 615 turns on the air-conditioning apparatus 630, and the process proceeds to step S708 (step S709). On the other hand, if the air-conditioning apparatus 630 is on, and the process proceeds to step S708 with step S709 omitted. In step S708, the controller 615 decreases the set temperature for the air-conditioning apparatus 630.

The above-described air-conditioning control is only an example and does not limit the air-conditioning control according to the present embodiment. For example, if the thermal sensation determining unit 104 makes the thermal sensation determination at a relatively short period, the system is expected to bear a heavy burden when air-conditioning control is performed every time the thermal sensation determination Xnew is provided. In this case, the air-conditioning control may be performed at a period longer than that at which the thermal sensation determination is made. Furthermore, in the above-described example, the set temperature is controlled. However, when the air-conditioning control is performed at a period shorter than that at which the thermal sensation actually felt by the subject varies, the temperature may become too high or low. In this case, the control of the set temperature may be omitted or performed at a period longer than that at which the air-conditioning apparatus 630 is turned on and off. Additionally, the controller 615 may control the wind speed or direction of the air-conditioning apparatus 630 on the basis of the thermal sensation determination value Xnew obtained by the thermal sensation determining unit 104.

As described above, the air-conditioning control apparatus according to the present embodiment controls the air-conditioning apparatus on the basis of the thermal sensation determination result. The present embodiment can therefore automatically perform such air-conditioning control as felt comfortable by the subject. Furthermore, controlling the turning-on and -off of the air-conditioning apparatus makes it possible to avoid unnecessary operation of the air-conditioning apparatus. This contributes to saving energy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A thermal sensation determining apparatus comprising:
a skin temperature detecting unit configured to detect a skin temperature of a peripheral site of a subject's body;
a variation state determining unit configured to (a) determine a variation state determination result of the skin temperature during a first interval to be a first state if a difference between a maximum value and a minimum value of the skin temperature during the first interval is smaller than a temperature threshold or if the difference between the maximum value and the minimum value is equal to or greater than the temperature threshold and a time difference in detection time between the maximum value and the minimum value is equal to or greater than a first time threshold, (b) determine the variation state determination result to be a second state if the difference between the maximum value and the minimum value is equal to or greater than the temperature threshold and the time difference is smaller than the first time threshold and equal to or greater than a second time threshold which is smaller than the first time threshold, and (c) determine the variation state determination result to be a third state if the difference between the maximum value and the minimum value is equal to or greater than the temperature threshold and the time difference is smaller than the second time threshold;
a gradient detecting unit configured to detect a gradient of the skin temperature during a second interval longer than the first interval to (d) determine a gradient detection result to be a first gradient if the gradient of the skin temperature is equal to or greater than a first gradient threshold, (e) determine the gradient detection result to be a second gradient if the gradient of the skin temperature is equal to or greater than a second gradient threshold smaller than the first gradient threshold and is smaller than the first gradient threshold, and (f) determine the gradient detection result to be a third gradient if the gradient of the skin temperature is smaller than the second gradient threshold; and a thermal sensation determining unit configured to determine the subject's thermal sensation using an old thermal sensation determination result, the variation state determination result and the gradient detection result to obtain a new thermal sensation determination result classified into levels ranging from "hot" to "cold" based on a "moderate" temperature.

2. An air-conditioning control apparatus comprising:

a skin temperature detecting unit configured to detect a skin temperature of a peripheral site of a subject's body;

a variation state determining unit configured to (a) determine a variation state determination result of the skin temperature during a first interval to be a first state if a difference between a maximum value and a minimum value of the skin temperature during the first interval is smaller than a temperature threshold or if the difference between the maximum value and the minimum value is equal to or greater than the temperature threshold and a time difference in detection time between the maximum value and the minimum value is equal to or greater than a first time threshold, (b) determine the variation state determination result to be a second state if the difference between the maximum value and the minimum value is equal to or greater than the temperature threshold and the time difference is smaller than the first time threshold and equal to or greater than a second time threshold which is smaller than the first time threshold, and (c) determine the variation state determination result to be a third state if the difference between the maximum value and the minimum value is equal to or greater than the temperature threshold and the time difference is smaller than the second time threshold;

a gradient detecting unit configured to detect a gradient of the skin temperature during a second interval longer than the first interval to (d) determine a gradient detection result to be a first gradient if the gradient of the skin temperature is equal to or greater than a first gradient threshold, (e) determine the gradient detection result to be a second gradient if the gradient of the skin temperature is equal to or greater than a second gradient threshold smaller than the first gradient threshold and is smaller than the first gradient threshold, and (f) determine the gradient detection result to be a third gradient if the gradient of the skin temperature is smaller than the second gradient threshold;

a thermal sensation determining unit configured to determine the subject's thermal sensation using an old thermal sensation determination result, the variation state determination result and the gradient detection result to obtain a new thermal sensation determination result classified into levels ranging from "hot" to "cold" based on a "moderate" temperature; and a controller to control turning-on and -off of an air-conditioning apparatus based on the new thermal sensation determination result.

3. A thermal sensation determining apparatus comprising:

a skin temperature detecting unit configured to detect a skin temperature of a peripheral site of a subject's body;

a variation state determining unit configured to (a) determine a variation state determination result of the skin temperature during a first interval to be a first state if a difference between a maximum value and a minimum value of the skin temperature during the first interval is smaller than a temperature threshold or if the difference between the maximum value and the minimum value is equal to or greater than the temperature threshold and a time difference in detection time between the maximum value and the minimum value is equal to or greater than a first time threshold, (b) determine the variation state determination result to be a second state if the difference between the maximum value and the minimum value is equal to or greater than the temperature threshold and the time difference is smaller than the first time threshold and equal to or greater than a second time threshold which is smaller than the first time threshold, and (c) determine the variation state determination result to be a third state if the difference between the maximum value and the minimum value is equal to or greater than the temperature threshold and the time difference is smaller than the second time threshold;

a gradient detecting unit configured to detect a gradient of the skin temperature during a second interval longer than the first interval to (d) determine a gradient detection result to be a first gradient if a variance in the skin temperature during the second interval is equal to or greater than a variance threshold and the gradient is equal to or greater than a gradient threshold, (e) determine the gradient detection result to be a second gradient if the variance is smaller than the variance threshold, and (f) determine the gradient detection result to be a third gradient if the variance is equal to or greater than the variance threshold and the gradient is smaller than the gradient threshold; and a thermal sensation determining unit configured to determine the subject's thermal sensation using an old thermal sensation determination result, the variation state determination result and the gradient detection result to obtain a new thermal sensation determination result classified into levels ranging from "hot" to "cold" based on a "moderate" temperature.

4. A thermal sensation determining apparatus comprising:

a skin temperature detecting unit configured to detect a skin temperature of a peripheral site of a subject's body;

a variation state determining unit configured to perform frequency analysis on the skin temperature during a first interval to (a) determine a variation state determination result of the skin temperature during the first interval to be a first state if no peak in the frequency analysis result is present within a frequency range, (b) determine the variation state determination result to be a second state if the peak in the frequency analysis result is within the frequency range and within a range of frequencies lower than a frequency threshold, and (c) determine the variation state determination result to be a third state if the peak in the frequency analysis result is within the frequency range and within a range of frequencies equal to or greater than the frequency threshold;

a gradient detecting unit configured to detect a gradient of the skin temperature during a second interval longer than the first interval to (d) determine a gradient detection result to be a first gradient if the gradient of the skin temperature is equal to or greater than a first gradient threshold, (e) determine the gradient detection result to be a second gradient if the gradient of the skin temperature is equal to or greater than a second gradient threshold smaller than the first gradient threshold and is smaller than the first gradient threshold, and (f) determine the gradient detection result to be a third gradient if the gradient of the skin temperature is smaller than the second gradient threshold; and a thermal sensation determining unit configured to determine the subject's thermal sensation using an old thermal sensation determination result, the variation state determination result and the gradient detection result to obtain a new thermal sensation determination result classified into levels ranging from "hot" to "cold" based on a "moderate" temperature.

5. A thermal sensation determining apparatus comprising:
a skin temperature detecting unit configured to detect a skin temperature of a peripheral site of a subject's body;
a variation state determining unit configured to perform frequency analysis on the skin temperature during a first interval to (a) determine a variation state determination result of the skin temperature during the first interval to be a first state if no peak in the frequency analysis result is present within a frequency range, (b) determine the variation state determination result to be a second state if the peak in the frequency analysis result is within the frequency range and within a range of frequencies lower than a frequency threshold, and (c) determine the variation state determination result to be a third state if the peak in the frequency analysis result is within the frequency range and within a range of frequencies equal to or greater than the frequency threshold;
a gradient detecting unit configured to detect a gradient of the skin temperature during a second interval longer than the first interval to (d) determine a gradient detection result to be a first gradient if a variance in the skin temperature during the second interval is equal to or greater than a variance threshold and the gradient is equal to or greater than a gradient threshold, (e) determine the gradient detection result to be a second gradient if the variance is smaller than the variance threshold, and (f) determine the gradient detection result to be a third gradient if the variance is equal to or greater than the variance threshold and the gradient is smaller than the gradient threshold; and
a thermal sensation determining unit configured to determine the subject's thermal sensation using an old thermal sensation determination result, the variation state determination result and the gradient detection result to obtain a new thermal sensation determination result classified into levels ranging from "hot" to "cold" based on a "moderate" temperature.

6. An air-conditioning control apparatus comprising:
a skin temperature detecting unit configured to detect a skin temperature of a peripheral site of a subject's body;
a variation state determining unit configured to (a) determine a variation state determination result of the skin temperature during a first interval to be a first state if a difference between a maximum value and a minimum value of the skin temperature during the first interval is smaller than a temperature threshold or if the difference between the maximum value and the minimum value is equal to or greater than the temperature threshold and a time difference in detection time between the maximum value and the minimum value is equal to or greater than a first time threshold, (b) determine the variation state determination result to be a second state if the difference between the maximum value and the minimum value is equal to or greater than the temperature threshold and the time difference is smaller than the first time threshold and equal to or greater than a second time threshold which is smaller than the first time threshold, and (c) determine the variation state determination result to be a third state if the difference between the maximum value and the minimum value is equal to or greater than the temperature threshold and the time difference is smaller than the second time threshold;
a gradient detecting unit configured to detect a gradient of the skin temperature during a second interval longer than the first interval to (d) determine a gradient detection result to be a first gradient if a variance in the skin temperature during the second interval is equal to or greater than a variance threshold and the gradient is equal to or greater than a gradient threshold, (e) determine the gradient detection result to be a second gradient if the variance is smaller than the variance threshold, and (f) determine the gradient detection result to be a third gradient if the variance is equal to or greater than the variance threshold and the gradient is smaller than the gradient threshold;
a thermal sensation determining unit configured to determine the subject's thermal sensation using an old thermal sensation determination result the variation state determination result and the gradient detection result to obtain a new thermal sensation determination result classified into levels ranging from "hot" to "cold" based on a "moderate" temperature; and
a controller to control turning-on and -off of an air-conditioning apparatus based on the new thermal sensation determination result.

7. An air conditioning control apparatus comprising:
a skin temperature detecting unit configured to detect a skin temperature of a peripheral site of a subject's body;
a variation state determining unit configured to perform frequency analysis on the skin temperature during a first interval to (a) determine a variation state determination result of the skin temperature during the first interval to be a first state if no peak in the frequency analysis result is present within a frequency range, (b) determine the variation state determination result to be a second state if the peak in the frequency analysis result is within the frequency range and within a range of frequencies lower than a frequency threshold, and (c) determine the variation state determination result to be a third state if the peak in the frequency analysis result is within the frequency range and within a range of frequencies equal to or greater than the frequency threshold;
a gradient detecting unit configured to detect a gradient of the skin temperature during a second interval longer than the first interval to (d) determine a gradient detection result to be a first gradient if the gradient of the skin temperature is equal to or greater than a first gradient threshold, (e) determine the gradient detection result to be a second gradient if the gradient of the skin temperature is equal to or greater than a second gradient threshold smaller than the first gradient threshold and is smaller than the first gradient threshold, and (f) determine the gradient detection result to be a third gradient if the gradient of the skin temperature is smaller than the second gradient threshold;
a thermal sensation determining unit configured to determine the subject's thermal sensation using an old thermal sensation determination result the variation state determination result and the gradient detection result to obtain a new thermal sensation determination result classified into levels ranging from "hot" to "cold" based on a "moderate" temperature; and
a controller to control turning-on and -off of an air-conditioning apparatus based on the new thermal sensation determination result.

8. An air conditioning control apparatus comprising:
a skin temperature detecting unit configured to detect a skin temperature of a peripheral site of a subject's body;
a variation state determining unit configured to perform frequency analysis on the skin temperature during a first interval to (a) determine a variation state determination result of the skin temperature during the first interval to be a first state if no peak in the frequency analysis result is present within a frequency range, (b) determine the variation state determination result to be a second state if the peak in the frequency analysis result is within the frequency range and within a range of frequencies lower than a frequency threshold, and (c) determine the variation state determination result to be a third state if the peak in the frequency analysis result is within the frequency range and within a range of frequencies equal to or greater than the frequency threshold;
a gradient detecting unit configured to detect a gradient of the skin temperature during a second interval longer than the first interval to (d) determine a gradient detection result to be a first gradient if a variance in the skin temperature during the second interval is equal to or greater than a variance threshold and the gradient is equal to or greater than a gradient threshold, (e) determine the gradient detection result to be a second gradient if the variance is smaller than the variance threshold, and (f) determine the gradient detection result to be a third gradient if the variance is equal to or greater than the variance threshold and the gradient is smaller than the gradient threshold;
a thermal sensation determining unit configured to determine the subject's thermal sensation using an old thermal sensation determination result, the variation state determination result and the gradient detection result to obtain a new thermal sensation determination result classified into levels ranging from "hot" to "cold" based on a "moderate" temperature; and
a controller to control turning-on and -off of an air-conditioning apparatus based on the new thermal sensation determination result.

* * * * *